US012105275B2

(12) United States Patent
Masaki et al.

(10) Patent No.: US 12,105,275 B2
(45) Date of Patent: Oct. 1, 2024

(54) LIGHT SOURCE DEVICE, ENDOSCOPE SYSTEM, AND CONTROL METHOD FOR LIGHT SOURCE DEVICE

(71) Applicant: OLYMPUS CORPORATION, Tokyo (JP)

(72) Inventors: Takahiro Masaki, Hachioji (JP); Masahiro Nishio, Hachioji (JP); Susumu Hashimoto, Hachioji (JP); Satoshi Tanaka, Hachioji (JP); Takeshi Ito, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 862 days.

(21) Appl. No.: 17/209,478

(22) Filed: Mar. 23, 2021

(65) Prior Publication Data

US 2021/0208384 A1 Jul. 8, 2021

Related U.S. Application Data

(63) Continuation of application No. PCT/JP2018/035847, filed on Sep. 27, 2018.

(51) Int. Cl.
*A61B 1/06* (2006.01)
*G02B 23/24* (2006.01)
(Continued)

(52) U.S. Cl.
CPC ..... *G02B 23/2461* (2013.01); *G02B 23/2484* (2013.01); *H05B 47/14* (2020.01); *A61B 1/0661* (2013.01)

(58) Field of Classification Search
CPC ............ G02B 23/2461; G02B 23/2484; H05B 47/14; H05B 45/325; H05B 45/30;
(Continued)

(56) References Cited

U.S. PATENT DOCUMENTS

2003/0179281 A1* 9/2003 Kato ................. H04N 1/40025
347/246
2012/0016200 A1* 1/2012 Seto ....................... A61B 1/045
600/180
(Continued)

FOREIGN PATENT DOCUMENTS

CN 105357805 A 2/2016
JP H02-172183 A 7/1990
(Continued)

OTHER PUBLICATIONS

International Search Report dated Dec. 4, 2018 received in PCT/JP2018/035847.

*Primary Examiner* — Howard D Brown, Jr.
(74) *Attorney, Agent, or Firm* — Scully, Scott, Murphy & Presser, P.C.

(57) ABSTRACT

A light source device includes a semiconductor light source that radiates light at a light quantity according to an applied current, a circuit that determines a current instruction value based on control information, first and second drive units, each of the units that is connected to the semiconductor light source and the circuit, and is capable of outputting, to the semiconductor light source, a current having magnitude corresponding to the current instruction value. The control information is set based on brightness of an image captured by an imaging element. When one of the first and second drive units is switched to the other, the circuit causes the other to start the current output after an elapse of a predetermined stop time period having a length at a predetermined ratio or less to a frame rate on the imaging element since a stop of the current output from the one.

20 Claims, 17 Drawing Sheets

(51) Int. Cl.
*G02B 23/26* (2006.01)
*H05B 47/14* (2020.01)

(58) Field of Classification Search
CPC . H05B 47/105; A61B 1/0661; A61B 1/00006; A61B 1/0638; A61B 1/0655; A61B 1/0684; A61B 1/0669
See application file for complete search history.

(56) References Cited

U.S. PATENT DOCUMENTS

| | | | |
|---|---|---|---|
| 2013/0214750 A1* | 8/2013 | Deboy | G05F 1/46 323/271 |
| 2013/0345517 A1* | 12/2013 | Morimoto | A61B 1/0638 600/178 |
| 2016/0360582 A1* | 12/2016 | Kato | H02M 1/32 |
| 2017/0105258 A1* | 4/2017 | Sakai | A61B 1/0661 |
| 2017/0202431 A1* | 7/2017 | Tanaka | G02B 23/26 |
| 2017/0258307 A1* | 9/2017 | Daidoji | A61B 1/00006 |
| 2017/0264078 A1* | 9/2017 | Daidoji | A61B 1/06 |
| 2018/0063925 A1* | 3/2018 | Nakayama | A61B 1/00165 |
| 2018/0368671 A1* | 12/2018 | Nakayama | A61B 1/0676 |
| 2019/0379178 A1* | 12/2019 | Muramatsu | H01S 5/06804 |
| 2021/0208384 A1* | 7/2021 | Masaki | A61B 1/0655 |

FOREIGN PATENT DOCUMENTS

| | | |
|---|---|---|
| JP | H10-144476 A | 5/1998 |
| JP | 2010-287544 A | 12/2010 |
| JP | 2012-019982 A | 2/2012 |
| JP | 2012-100887 A | 5/2012 |
| JP | 2015-065738 A | 4/2015 |
| JP | 2015-226340 A | 12/2015 |

* cited by examiner

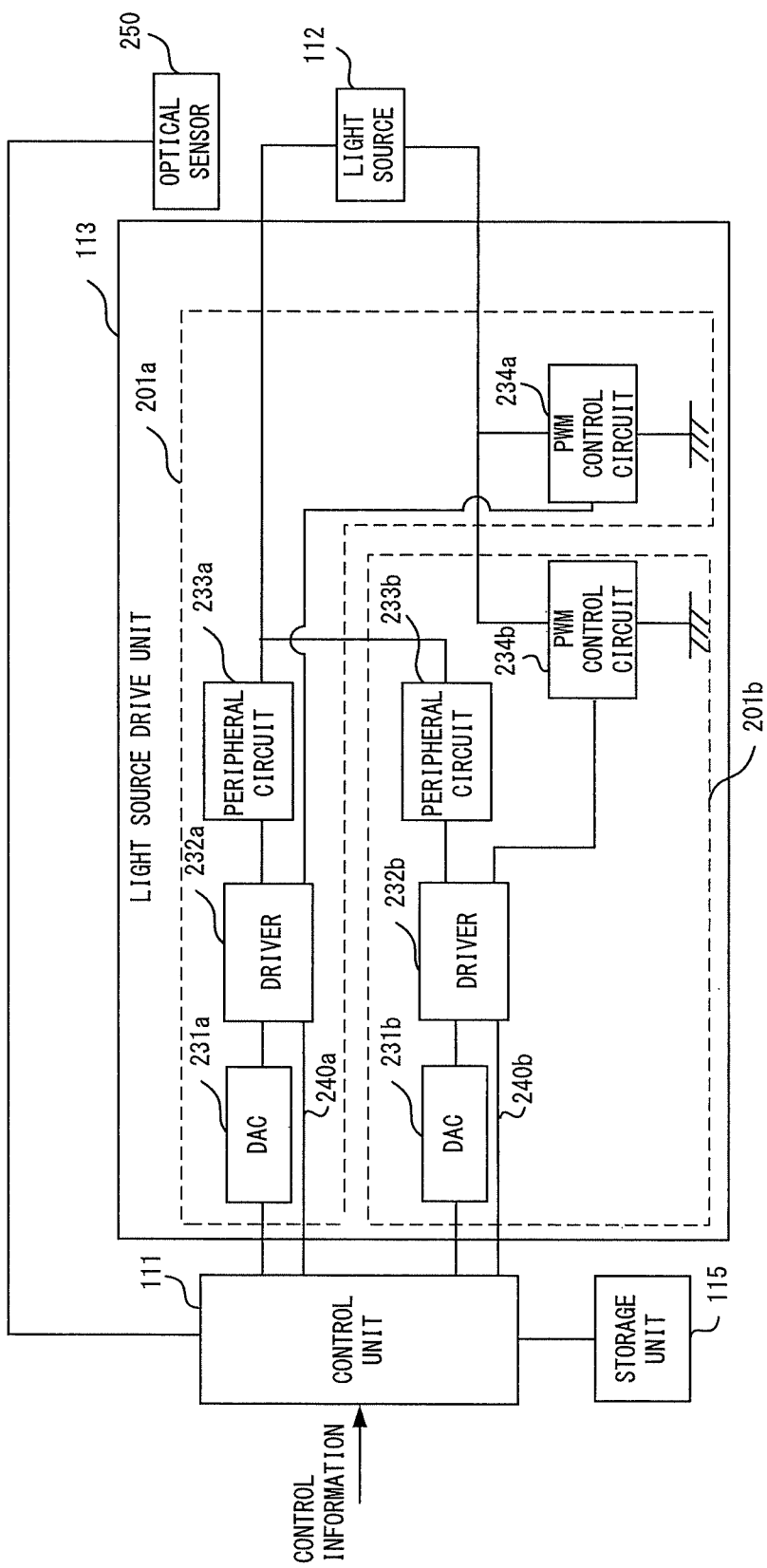
F I G. 2

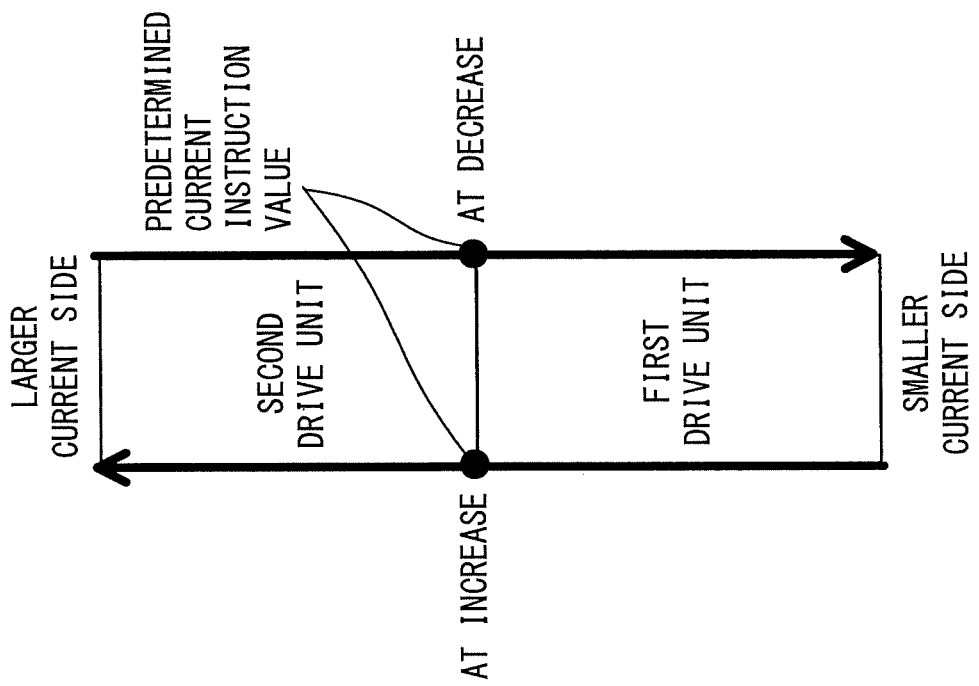

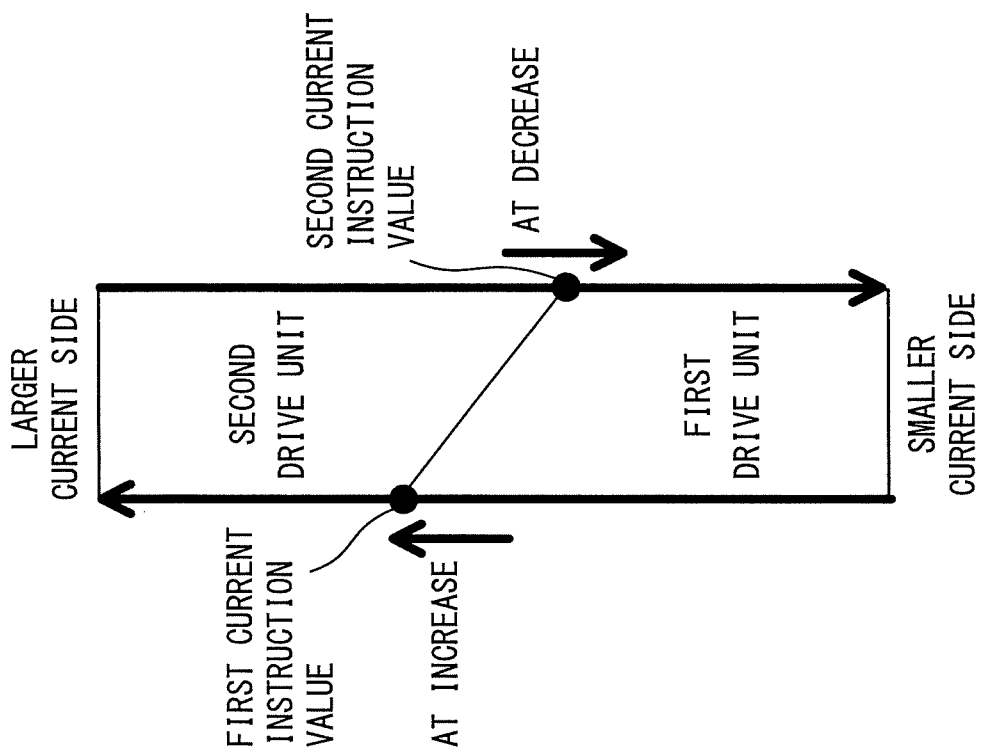

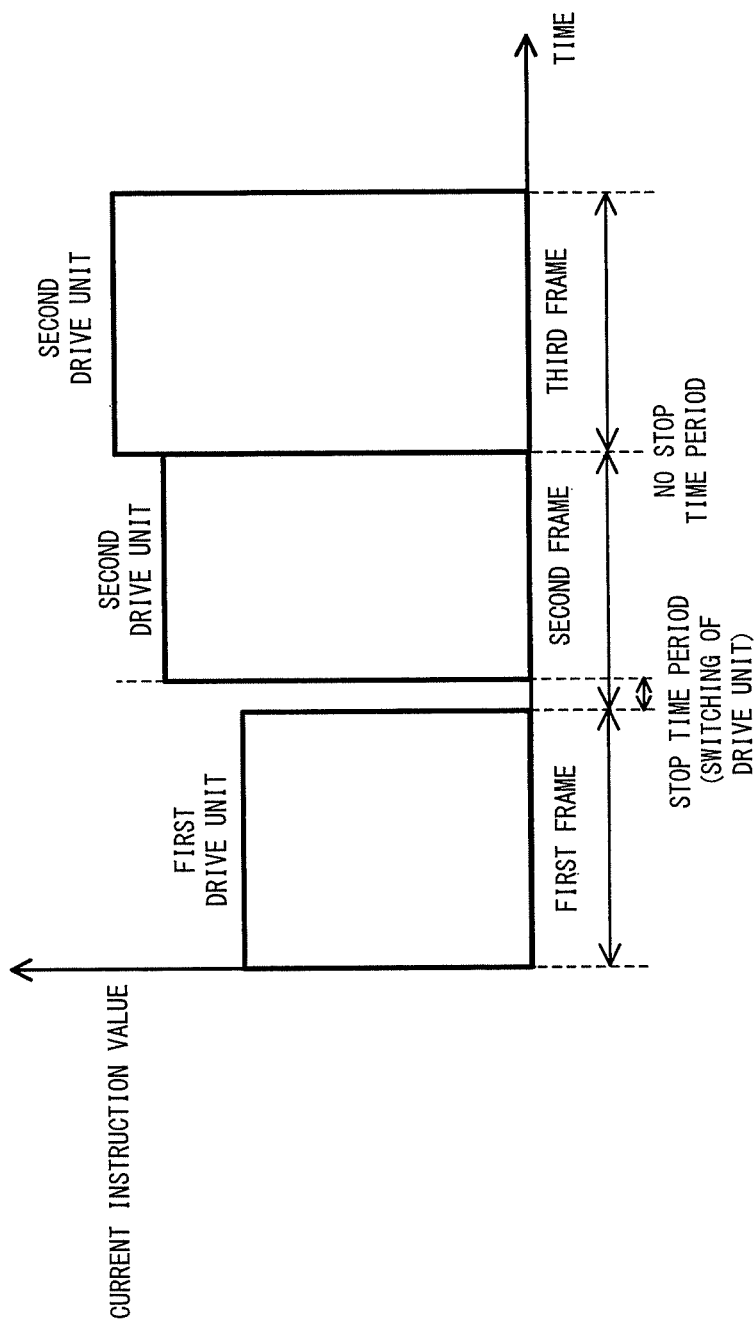
F I G. 10

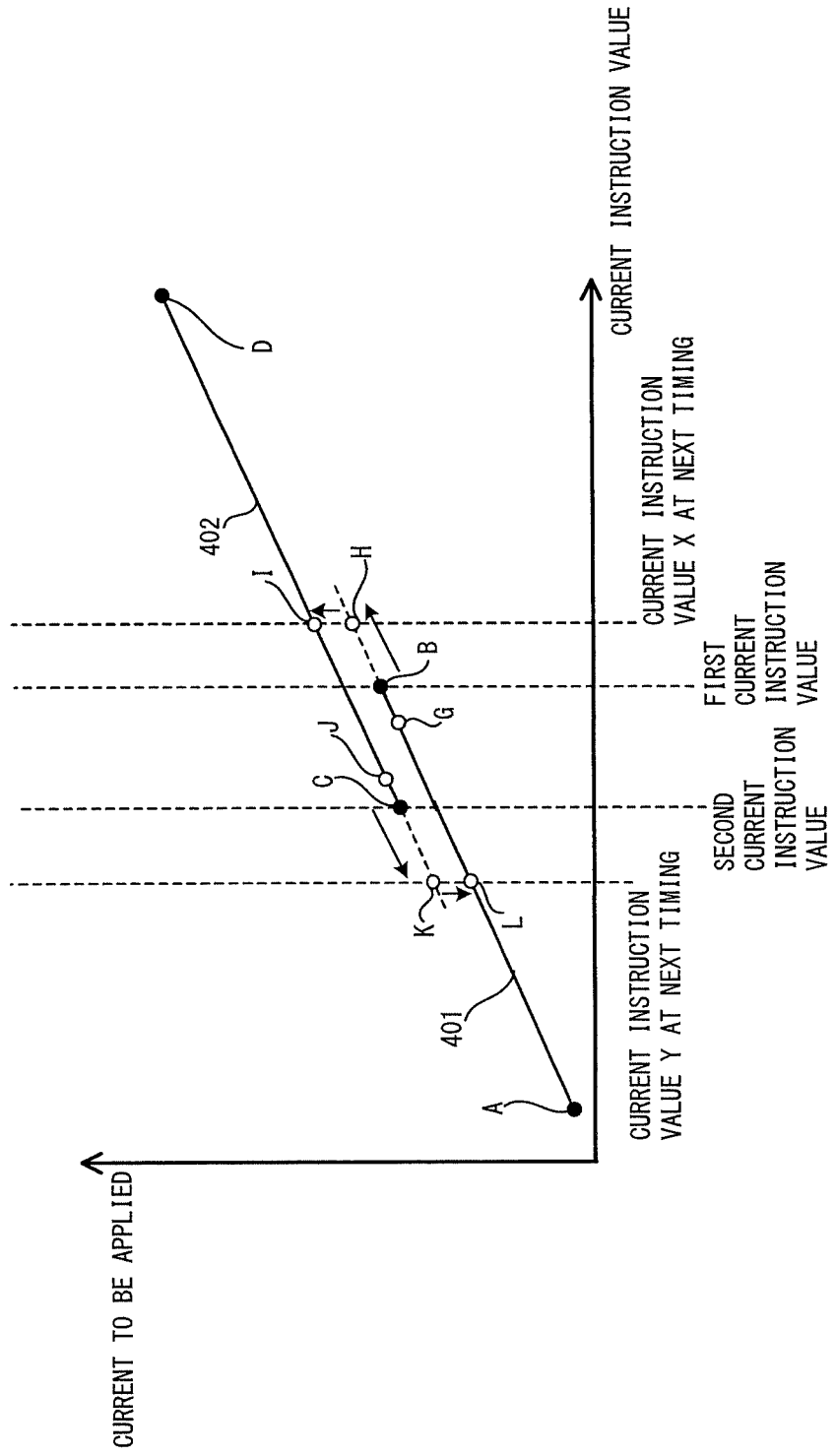
F I G. 12

LIGHT SOURCE DEVICE, ENDOSCOPE SYSTEM, AND CONTROL METHOD FOR LIGHT SOURCE DEVICE

CROSS REFERENCE TO RELATED APPLICATIONS

This is a Continuation Application of PCT Application No. PCT/JP2018/035847, filed Sep. 27, 2018, which was not published under PCT Article 21(2) in English.

BACKGROUND OF THE INVENTION

Field of the Invention

The present invention relates to a light source device, an endoscope system, and a control method for the light source device.

Description of the Related Art

An endoscope is widely used to observe a site to be examined such as an inner surface of a body cavity, and a surface of an organ, or to administer various types of treatment. In the endoscope, a light source device is used to capture an image of a site to be examined. In the light source device of the endoscope, a solid-state light source is increasingly coming into use as the light source. In the solid-state light source, a light quantity can be adjusted according to a current to be applied. In recent years, a semiconductor light source such as a light emitting diode (LED) that can emit a large quantity of light by applying a large current has been used.

The light source device adjusts the light quantity emitted by the light source by controlling the current to be applied to the light source, for example. In this regard, a technology related to the adjustment of the current to be applied to the light source has been known (for example, Japanese Patent Laid-Open No. 2010-287544, Japanese Patent Laid-Open No. 2012-19982, Japanese Patent Laid-Open No. 2012-100887, Chinese Patent No. 105357805).

SUMMARY OF THE INVENTION

A light source device of one aspect of the present invention includes a semiconductor light source that radiates light at a light quantity according to a current to be applied, a control circuit that determines a current instruction value based on input control information, a first drive unit that is connected to the semiconductor light source and the control circuit, and is capable of outputting, to the semiconductor light source, a current having magnitude corresponding to the current instruction value, and a second drive unit that is connected to the semiconductor light source and the control circuit, and is capable of outputting, to the semiconductor light source, a current having magnitude corresponding to the current instruction value. A minimum current value to be output by the first drive unit is smaller than a minimum current value to be output by the second drive unit. A maximum current value to be output by the first drive unit is smaller than a maximum current value to be output by the second drive unit, and is larger than the minimum current value to be output by the second drive unit.

An endoscope system of one aspect of the present invention includes an endoscope, a semiconductor light source that supplies, to the endoscope, light at a light quantity according to a current to be applied, a control circuit that determines a current instruction value based on input control information, a first drive unit that is connected to the semiconductor light source and the control circuit, and is capable of outputting, to the semiconductor light source, a current having magnitude corresponding to the current instruction value, and a second drive unit that is connected to the semiconductor light source and the control circuit, and is capable of outputting, to the semiconductor light source, a current having magnitude corresponding to the current instruction value. The control information is set based on brightness of a captured image captured by an imaging element of the endoscope, and when one drive unit of the first drive unit and the second drive unit is switched to the other drive unit, the control circuit causes the other drive unit to start the output of the current to the semiconductor light source after an elapse of a predetermined stop time period having a length at a predetermined ratio or less with respect to a frame rate of imaging by the imaging element since a stop of the output of the current from the one drive unit to the semiconductor light source.

A control method for a light source device of one aspect of the present invention is a control method for a light source device that determines a current instruction value based on input control information and includes a first drive unit and a second drive unit each of which is capable of outputting, to a semiconductor light source, a current having magnitude corresponding to the current instruction value. The method includes setting the control information based on brightness of a captured image captured by an imaging element, and when one drive unit of the first drive unit and the second drive unit is switched to the other drive unit, causing the other drive unit to start an output of the current to the semiconductor light source after an elapse of a predetermined stop time period having a length at a predetermined ratio or less with respect to a frame rate of imaging by the imaging element since a stop of an output of the current from the one drive unit to the semiconductor light source.

BRIEF DESCRIPTION OF THE DRAWINGS

FIG. 2 is a diagram illustrating an example of a light source drive unit according to an embodiment.

FIGS. 3A and 3B each are a diagram for illustrating setting of switching conditions of a drive unit.

FIG. 10 is a graph showing a relationship between an imaging frame and a stop time period.

FIG. 12 is another graph showing a flow of a switching control of the drive unit according to an embodiment.

DETAILED DESCRIPTION OF THE PREFERRED EMBODIMENTS

Figure 1:
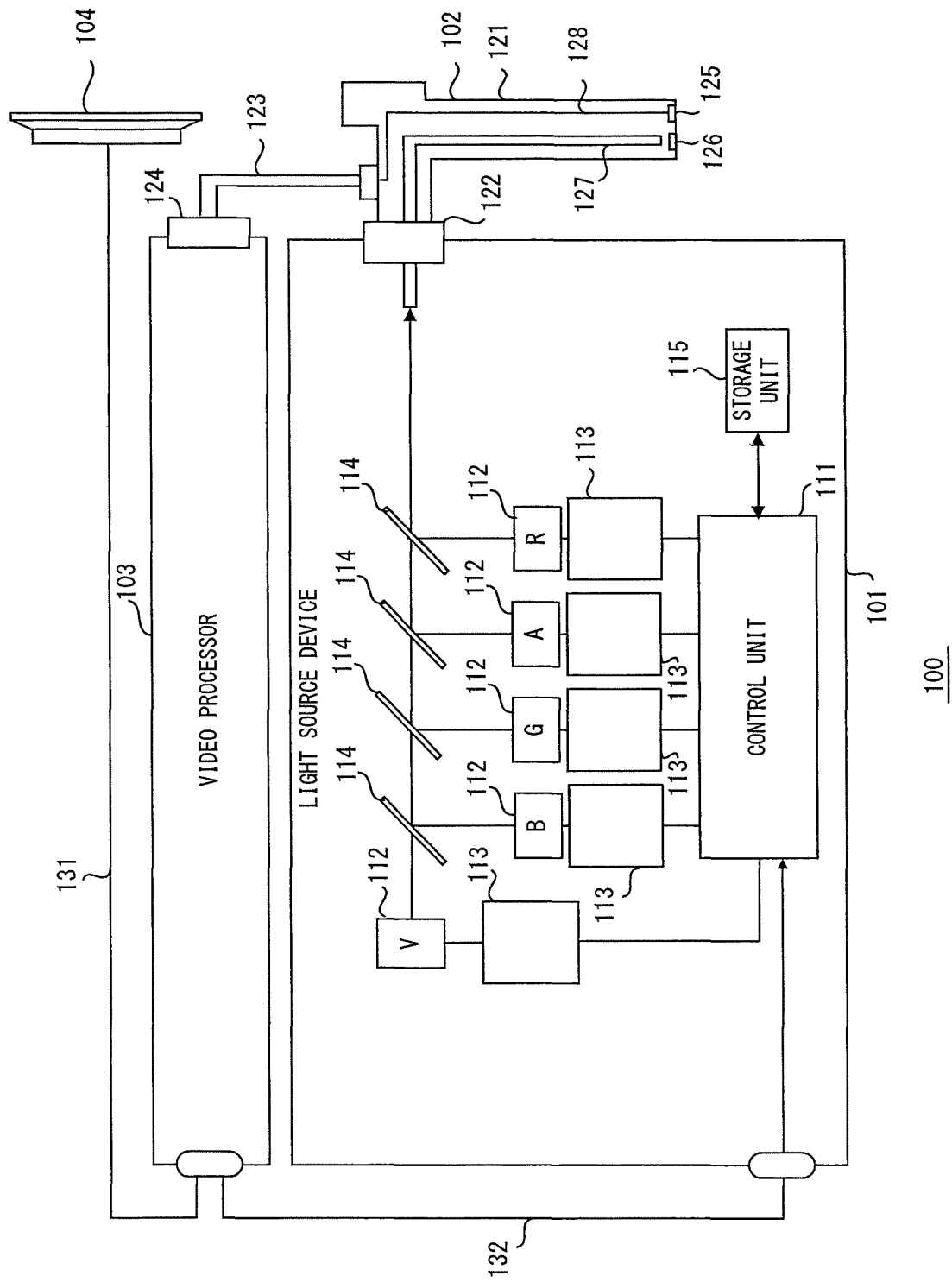
FIG. 1 is a diagram illustrating an endoscope system.

For example, when a semiconductor light source such as an LED that emits a large quantity of light is used as the light source, a light source device that can apply currents over a wide range of current values to the light source is required to emit the light in a desired light quantity adjustment range. It is desirable therefore to provide a light source device that can apply currents over a wide range of current values to the light source.

In view of the above-described circumstances, embodiments of the present invention will be described below.

Hereinafter, several embodiments of the present invention will be described in detail with reference to the drawings. Note that corresponding elements in a plurality of drawings are denoted with the same reference numeral.

FIG. 1 is a diagram illustrating an endoscope system 100. FIG. 1 illustrates in which a light source device 101 according to an embodiment is applied to the endoscope system 100.

The endoscope system 100 includes, for example, the light source device 101, an endoscope 102, a video processor 103, and a monitor 104. The endoscope 102 has, on a distal end side thereof, an elongated insertion portion 121 insertable into a lumen and the like, and a proximal end side thereof is detachably connected to the light source device 101 through a connector 122. The endoscope 102 is detachably connected to the video processor 103 through a cable 123 and the connector 124. Therefore, in the endoscope system 100, various types of endoscope 102 can be attached to the light source device 101 and the video processor 103.

The distal end of the insertion portion 121 is provided with an imaging element 125 for capturing a video image of a site to be examined such as an inner surface of a body cavity, and a surface of an organ and a lens 126 for emitting the light from the light source device 101 to the site to be examined. The light transmitted from the light source device 101 through a light guide 127 is emitted to the site to be examined through the lens 126.

The imaging element 125 is configured by, for example, a charged-coupled devices (CCD) sensor, a complementary metal-oxide-semiconductor (CMOS) sensor, or the like. The imaging element 125 operates when a drive signal including a synchronization signal is supplied from the video processor 103. The return light of the light emitted from the lens 126 to the site to be examined enters an imaging surface of the imaging element 125. The imaging element 125 performs photoelectric conversion on the optical image of the site to be examined, the optical image being incident thereon, and supplies an imaging output based on accumulated charge to the video processor 103 through a signal line 128.

The video processor 103 performs a predetermined signal processing on the imaging output, and generates a video image signal displayable on the monitor 104. The video image signal from the video processor 103 is supplied to the monitor 104 through the cable 131. The monitor 104 displays, on a display screen, an endoscope image based on the supplied imaging output.

The video processor 103 controls the light source device 101 so that the brightness of the captured image becomes target brightness, for example. For example, the video processor 103 outputs, to the light source device 101, control information indicating the adjustment amount of the light quantity for adjusting the brightness of the captured image to predetermined target brightness. The control information is supplied to a control unit 111 of the light source device 101 through a cable 132.

The light source device 101 includes, for example, the control unit 111, a light source 112, a light source drive unit 113, and a dichroic mirror 114. The control unit 111 may be a circuit that performs an operation, and may be, for example, a control circuit such as a field programmable gate array (FPGA) or a processor.

The light source 112 may be, for example, a semiconductor light source such as an LED or a semiconductor laser (LD: laser diode) that radiates the light at a light quantity according to a current to be applied. Note that FIG. 1 illustrates an example in which the light source device 101 includes five light sources 112 in violet (V), blue (B), green (G), amber (A), and red (R) colors, but the embodiment is not limited thereto. In another embodiment, the light source device 101 may include more than five light sources 112 or less than five light sources 112. In addition, the colors of the light sources 112 are not limited to the above-described colors, and do not necessarily include some colors or may be the other colors. In an example, the number of the light sources 112 included in the light source device 101 may be one.

For example, the type and the number of the light sources 112 included in the light source device 101 and the type and the number of light sources that are caused to emit the light by the control unit 111 of the light source device 101 may vary depending on applications of the light source device 101. For example, in the endoscope system 100, the light sources 112 caused to emit the light are controlled according to an object to be observed. For example, in the endoscope 102, as observation modes, there are known white-light observation (WLI: white-light imaging), and observation using special light referred to as narrow-band light observation (NBI: Narrow band imaging) and autofluorescence observation (AFI: Autofluorescence imaging).

In the white-light observation (WLI), the control unit 111 controls the light sources 112 of the five colors: violet (V), blue (B), green (G), amber (A), and red (R) to be caused to emit the light. The narrow-band observation (NBI) is an observation mode for observing a blood vessel with good contrast, and the control unit 111 causes only the light sources 112 of violet (V) and green (G) to emit the light. The autofluorescence observation (AFI) is an observation mode for observing autofluorescence, and the control unit 111 causes only the light sources 112 of violet (V) and green (G) to emit the light, but the autofluorescence observation (AFI) is different from the narrow-band observation (NBI) in a light quantity ratio of violet (V) to green (G).

For example, the light emitted from each light source 112 may be converted into substantially parallel light by the lens and then emitted. The dichroic mirrors 114 are disposed on respective optical axes of the emitted light from the light sources 112. For example, the dichroic mirrors 114 each have characteristics of reflecting the light having a particular wavelength and transmitting the light having the other wavelengths, and combine the light from each light source 112. For example, the dichroic mirror 114 at a left end in FIG. 1 transmits the emitted light from the light source 112 that emits the light of violet (V) and reflects the emitted light from the light source 112 that emits the light of blue (B), to combine the emitted light of violet (V) and the emitted light of blue (B). For example, the combined light from the dichroic mirror 114 enters the light guide 127 through the lenses, and is emitted to the site to be examined. Note that the arrangement of the light sources 112 of the respective colors in FIG. 1 is an illustrative example, and can be changed to various arrangements by appropriately setting the characteristics of the dichroic mirror 114.

Each light source 112 is driven when a current is applied thereto from the corresponding light source drive unit 113 corresponding, and then is lit. The light source drive unit 113 applies the current to the corresponding light source 112 under the control by the control unit 111. For example, each light source 112 emits the light with a light emitting quantity corresponding to the current applied from the corresponding light source drive unit 113. For example, the control unit 111 outputs a current instruction value for controlling each light source 112 to the corresponding light source drive unit 113 to thereby control a level of the current to be applied from the light source drive unit 113 so that the light quantity of each light source 112 is controlled. Note that in the light source 112, a minimum current value that can ensure stable light emission and a maximum current value that reflects safety, product life and the like may be defined. In one embodiment, regarding the minimum current value, the control unit 111 may control the light source drive unit 113 to cause the light source drive unit 113 to supply a current below the minimum current value. Furthermore, regarding the maximum current value, the control unit 111 may control the light source drive unit 113 so that a current exceeding the maximum current value is not supplied to the light source 112.

The light emission and light quantity of each light source 112 can be individually controlled. The control unit 111 is electrically connected to the light source drive units 113 that are connected to the respective light sources 112, and may control the light quality ratio, the light emission timing, and the like in conjunction with each light source 112. For example, the video processor 103 outputs, to the control unit 111 of the light source device 101, the control information indicating the adjustment amount for adjusting the light quantity of the captured image to be output to the monitor 104 to reach a predetermined target light quantity with which the captured image is easier to view than the current image for a user, based on the imaging output captured by the imaging element 125. For example, the control unit 111 of the light source device 101 outputs the current instruction value to each light source drive unit 113 according to the control information input from the video processor 103, and the light source drive unit 113 applies, to the corresponding light source 112, the current corresponding to the input current instruction value, whereby the quantity of the light emitted by the light source 112 is controlled.

A storage unit 115 of the light source device 101 may be, for example, a storage device such as a memory, and may include a RAM region and a ROM region. Note that RAM is the abbreviation for Random Access Memory. In addition, ROM is the abbreviation for Read Only Memory.

As described above, in recent years, an LED that can emit a large quantity of light by applying a large current has been used. It is desirable to provide the light source device 101 that can apply the current over a wide current range to the light source 112, to emit, from the light source 112, the light over a wide range including a large light quantity. In the embodiment, the light source drive unit 113 includes a plurality of drive units 201 that can apply, to one light source 112, currents in different ranges, respectively.

FIG. 2 is a diagram illustrating an example of the light source drive unit 113 according to the embodiment. FIG. 2 illustrates the control unit 111, the light source 112, the light source drive unit 113, the storage unit 115, and an optical sensor 250. Note that FIG. 2 illustrates the light source drive unit 113, the light source 112, and the optical sensor 250 that form one set, but when the light source device 101 includes a plurality of light sources 112 as illustrated in FIG. 1, the control unit 111 may be connected with a plurality of sets of the light source drive unit 113, the light source 112, and the optical sensor 250.

For example, the control unit 111 of the light source device 101 determines the current instruction value for specifying a current to be applied to the light source 112 according to the control information indicating the adjustment amount of the light quantity input from the video processor 103. Note that in another embodiment, the control unit 111 may determine the current instruction value for specifying the current to be applied to the light source 112 further using the information indicating the current light quantity of the light source 112 detected by the optical sensor 250 in addition to the control information input from the video processor 103, for example. In one example, the light quantity of the light source 112 detected by the optical sensor 250 is used to adjust the light quantity of the light source 112 or to adjust the balance of the light quantity among the plurality of light sources 112 included in the light source device 101.

The current instruction value may be, for example, a digital value corresponding to a current in the current range that can be output from the light source drive unit 113 to the light source 112, and in one example, the current instruction value may be designated by values of 0000 to FFFF.

The light source drive unit 113 includes the plurality of drive units 201 configured to apply, to the light source 112, currents in different current ranges, respectively. The drive unit 201 is, for example, a drive circuit that drives the light source 112 by outputting a current having the magnitude corresponding to the current instruction value to the light source 112. The plurality of drive units 201 are configured to apply the currents in the different current ranges, respectively, whereby the light source drive unit 113 can apply the current at a current value over a wide range to the light source 112 such as an LED that emits a large quantity of light. FIG. 2 illustrates an example in which the light source drive unit 113 includes the two drive units 201 of a first drive unit 201a and a second drive unit 201b. Hereinafter, the description will be made by way of an example in which the two drive units 201 are used. However, the embodiment is not limited thereto, and the light source drive unit 113 may include three or more drive units 201 configured to apply, to the light source 112, the currents in different current ranges, respectively.

In FIG. 2, for example, the second drive unit 201b may be configured to apply, to the light source 112, a current in a current range on a larger current side than the current range of the first drive unit 201a. In other words, the maximum current value output by the first drive unit 201a may be smaller than the maximum current value output by the second drive unit 201b. In addition, the minimum current value output by the first drive unit 201a may be smaller than the minimum current value output by the second drive unit 201b. Furthermore, the output current range of the first drive unit 201a may overlap with the output current range of the second drive unit 201b. For example, the maximum current value output by the first drive unit 201a may be larger than the minimum current value output by the second drive unit 201b. Note that the maximum current value output by the drive unit 201 may be, for example, a maximum value of a current that can be output by the drive unit 201. In addition, the minimum current value output by the drive unit 201 may be, for example, a minimum value of a current that can be output by the drive unit 201. For example, the drive unit 201 may be configured to output the current in a predetermined current range according to the circuit configuration and setting of the drive unit 201 and the circuit configuration and setting of the light source drive unit 113 in which the drive unit 201 is mounted. In this case, the maximum current value may be, for example, a current which is the maximum value in the predetermined current range. In addition, the minimum current value may be, for example, a current which is the minimum value in the predetermined current range.

As illustrated in FIG. 2, the drive unit 201 (for example, the first drive unit 201a and the second drive unit 201b) include, for example, a digital-analog converter (DAC) 231, the driver 232, a peripheral circuit 233, and a pulse width modulation (PWM) control circuit 234. Note that in the example in FIG. 2, a suffix "a" is added to the reference numeral indicating each component included in the first drive unit 201a, and a suffix "b" is added to the reference numeral indicating each component included in the second drive unit 201b.

In the embodiment, for example, the control unit 111 selects any one of the first drive unit 201a and the second drive unit 201b based on the current instruction value at next timing specified based on the control information indicating the adjustment amount of the light quantity, and the currently selected drive unit 201. Note that the current instruction value is, for example, a value corresponding to a current to be applied to the light source 112.

Subsequently, the control unit 111 causes the selected drive unit 201 to apply, to the light source 112, the current having the magnitude corresponding to the current instruction value. For example, the control unit 111 converts a current instruction value at the next timing to the individual current instruction value indicating the current value corresponding to the current instruction value for the selected drive unit 201. Then, the control unit 111 outputs a signal indicating that the drive unit 201 is selected, to the selected drive unit 201 through a signal line 240, and outputs the converted individual current instruction value to the digital-analog converter 231 of the selected drive unit 201. The digital-analog converter 231 converts the individual current instruction value to a signal receivable by a driver 232, and supplies it to the driver 232. The driver 232 outputs a drive current for driving the light source 112 according to the signal transmitted from the digital-analog converter 231. Note that the digital-analog converter 231 can select, for example, the setting of channel (CH) used in the data signal and the reference voltage. In this case, for example, when the external noise overlaps with the data value to be transmitted from the control unit 111 to the digital-analog converter 231, the data value changes, and the selection of the reference voltage may change. As a result, the digital-analog converter 231 does not operate normally in some cases. Therefore, the update period of the data to be transmitted to the digital-analog converter 231 may be set in view of the above description.

The peripheral circuit 233 is electrically connected to the driver 232 of the corresponding drive unit 201. After amplifying the drive current output from the driver 232 at a predetermined ratio and performing smoothing and noise removal of the output current, the peripheral circuit 233 supplies the drive current to the light source 112. The light source 112 emits the light at the brightness according to the supplied drive current.

The PWM control circuit 234 is electrically connected to the driver 232 of the corresponding drive unit 201. The PWM control circuit 234 receives the control signal from the driver 232 of the corresponding drive unit 201, and performs the PWM. The PWM is a technology for adjusting the light quantity according to the period of time in which the light is emitted.

For example, the storage unit 115 may store the information to which the control unit 111 refers, to drive the light source 112 while switching between the two drive units 201. In one example, the storage unit 115 may store a first current instruction value and a second current instruction value, which will be described later.

The optical sensor 250 receives the light emitted from the light source 112, and outputs, to the control unit 111, the signal corresponding to the light quantity. For example, the control unit 111 may adjust the light quantity of the light source 112 and adjust the balance of the light quantity among the plurality of light sources 112 based on the signal corresponding to the light quantity input from the optical sensor 250.

Note that in one embodiment, the driver 232a and the driver 232b may have the same circuit configuration. In the driver 232a and the driver 232b having the same circuit configuration, a change in environment such as ambient temperature and a deterioration vary in the approximately same tendency. This can suppress a large change in the relationship that occurs due to the change in environment, the deterioration, or the like, the large change including a fact that the magnitude relationship such as conditions (will be described later) for switching between the first drive unit 201a and the second drive unit 201b, and the like is reversed. Even in this case, for example, the currents in the current ranges different between the first drive unit 201a and the second drive unit 201b can be applied to the light source 112 by setting the amplification ratio of the current by the peripheral circuit 233b in the second drive unit 201b to be larger than the amplification ratio of the current by the peripheral circuit 233a in the first drive unit 201a.

Subsequently, the switching conditions for switching between the first drive unit 201a and the second drive unit 201b will be described.

FIGS. 3A and 3B each are a diagram for illustrating setting of the switching conditions of the drive unit 201. As described above, in the embodiment, the currents over a wide range of current values are supplied to the light source 112 by switching between the first drive unit 201a that applies, to the light source 112, the current in the current range on the smaller current side and the second drive unit 201b that applies, to the light source 112, the current in the current range on the larger current side than the current range of the first drive unit 201a.

Here, for example, a predetermined value is used as the current instruction value for switching from the first drive unit 201a to the second drive unit 201b and switching from the second drive unit 201b to the first drive unit 201a, and the control unit 111 switches at the predetermined value (FIG. 3A). In this case, for example, when the current instruction value is changed across the predetermined value, the drive unit 201 is switched. However, for example, when the current instruction value is repeatedly changed around the predetermined value, it is not preferable because the drive unit 201 is frequently switched.

Therefore, in the embodiment, for example, a first current instruction value is used for switching from the first drive unit 201a to the second drive unit 201b, and a second current instruction value that is different from the first current instruction value is used for switching from the second drive unit 201b to the first drive unit 201a (FIG. 3B). Note that the first current instruction value may be a current instruction value for specifying the current on the larger current side than the second current instruction value. This makes it possible to achieve the so-called hysteresis, and can suppress that the switching between the first drive unit 201a and the second drive unit 201b is frequently performed. Note that the first current instruction value and the second current instruction value may be stored in the storage unit 115, for example. The control unit 111 may control the switching between the first drive unit 201a and the second drive unit 201b with reference to the first current instruction value and the second current instruction value that are stored in the storage unit 115.

Subsequently, the description will be made of an example in which the switching of the drive unit 201 is controlled using the above-described first current instruction value and second current instruction value.

Figure 4:
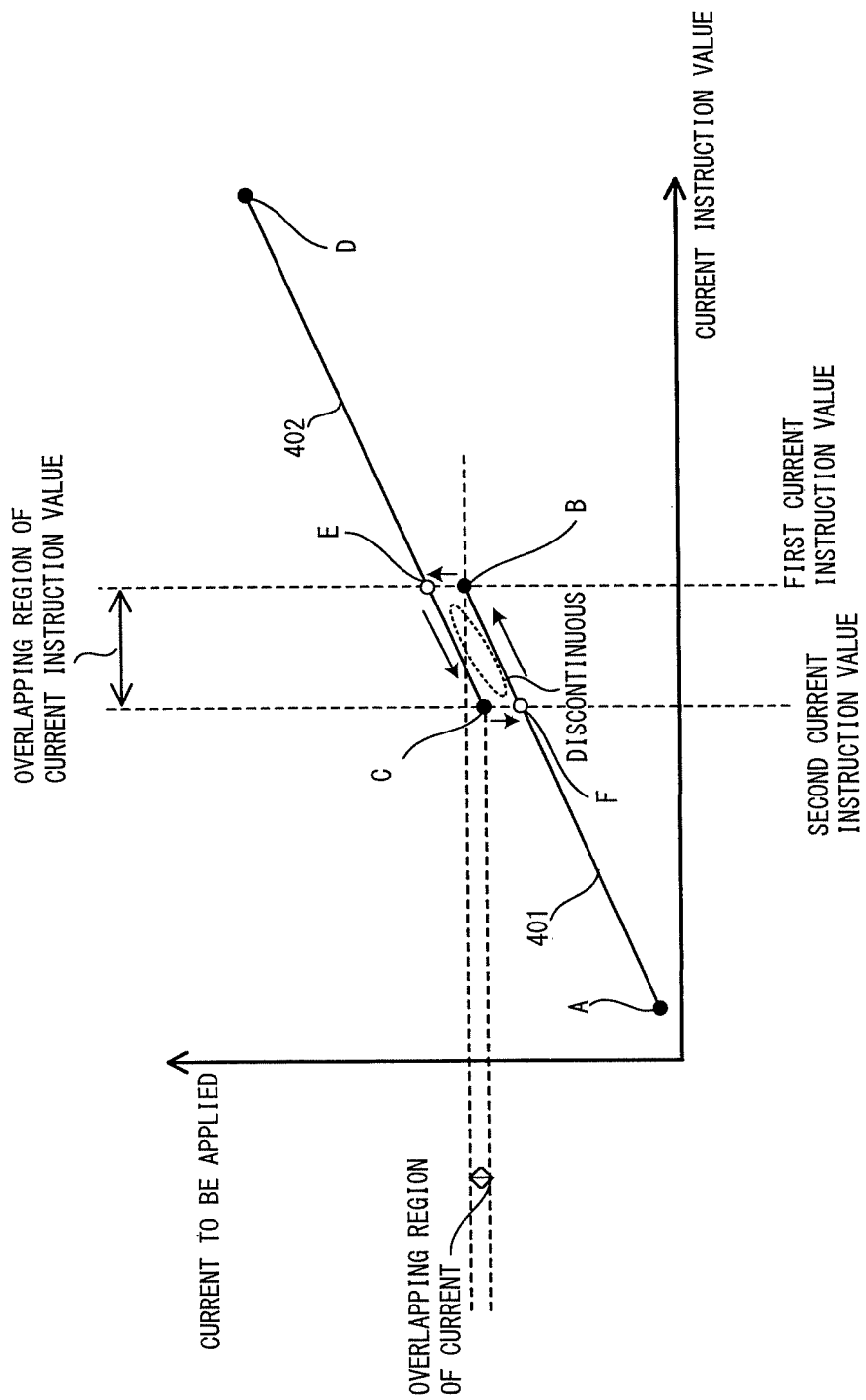
FIG. 4 is a graph showing a flow of a switching control of the drive unit according to the embodiment.

FIG. 4 is a graph showing a flow of the switching control of the drive unit 201 according to the embodiment. In FIG. 4, the vertical axis represents a current to be applied to the light source 112 from the drive unit 201. In addition, the horizontal axis represents the current instruction value.

FIG. 4 shows a first line segment 401 from a point A to a point B showing a correspondence relation between a current output by the first drive unit 201a and the current instruction value, and a second line segment 402 from a point C to a point D showing a correspondence relation between a current output by the second drive unit 201b and the current instruction value. For example, the first drive unit 201a may be configured to output the currents in the current range shown by the first line segment 401, and outputs a current corresponding, on the first line segment 401, to a current instruction value in a current instruction value range shown by the first line segment 401. Similarly, for example, the second drive unit 201b may be configured to output the currents in the current range shown by the second line segment 402, and outputs a current corresponding, on the second line segment 402, to a current instruction value in a current instruction value range shown by the second line segment 402.

As shown in FIG. 4, in the current instruction values represented by the horizontal axis, the first line segment 401 for the first drive unit 201a and the second line segment 402 for the second drive unit 201b have an overlapping region of the current instruction values between a range of the first current instruction values and a range of the second current instruction values.

Here, for example, it is assumed that the control unit 111 gradually changes the current instruction value from a certain current instruction value on the first line segment 401 in a direction of increasing the current, in a state in which the current is applied to the light source 112 from the first drive unit 201a. In this case, when the current instruction value becomes a first current instruction value (point B), the control unit 111 switches from the first drive unit 201a to the second drive unit 201b, and causes the second drive unit 201b to apply, to the light source 112, the current corresponding to a point E on the second line segment 402 at the first current instruction value.

On the other hand, for example, it is assumed that the control unit 111 gradually changes the current instruction value from a certain current instruction value on the second line segment 402 in a direction of decreasing the current, in a state in which the current is applied to the light source 112 from the second drive unit 201b. In this case, when the current instruction value becomes a second current instruction value (point C), the control unit 111 switches from the second drive unit 201b to the first drive unit 201a, and causes the first drive unit 201a to apply, to the light source 112, the current corresponding to a point F on the first line segment 401 at the second current instruction value. By providing an overlap of current instruction values between a range of the first current instruction values and a range of the second current instruction values in this way, the so-called hysteresis described above is achieved.

In the embodiment, as shown in FIG. 4, in the vertical axis, the first line segment 401 for the first drive unit 201a and the second line segment 402 for the second drive unit 201b have an overlapping region of the currents in the current range between the current corresponding to the first current instruction value and the current corresponding to the second current instruction value. That is, the current corresponding to the point C on the second line segment 402 at the second current instruction value at which the second drive unit 201b is switched to the first drive unit 201a is set to be smaller than the current corresponding to the point B on the first line segment 401 at the first current instruction value at which the first drive unit 201a is switched to the second drive unit 201b. This makes it possible to continuously apply, to the light source 112, the currents in a range from the point A to the point D using the two drive units 201.

As shown in FIG. 4, for example, the current value (current value at the point E) output by the second drive unit 201b at the first current instruction value may be different from the current value (current value at point B) associated with the case where the current corresponding to the first current instruction value is output by the first drive unit 201a. Similarly, the current value (current value at the point F) output by the first drive unit 201a at the second current instruction value may be different from the current value (current value at point C) associated with the case where the current corresponding to the second current instruction value is output by the second drive unit 201b. In other words, the current output by the first drive unit 201a and the current output by the second drive unit 201b with respect to one current instruction value are not necessarily strictly the same. As shown in FIG. 4, a discontinuous gap may be provided between the first line segment 401 and the second line segment 402.

Even when the discontinuous gap is provided in this way, for example, defining the relationship between the current instruction value and each output current of the first drive unit 201a and the second drive unit 201b to satisfy the predetermined condition can mitigate user's unnatural feeling caused by the change in the light quantity of the light source 112 occurring when the drive unit 201 is switched. Hereinafter, the predetermined condition for mitigating the user's unnatural feeling at the time of switching will be described.

Figure 5A:
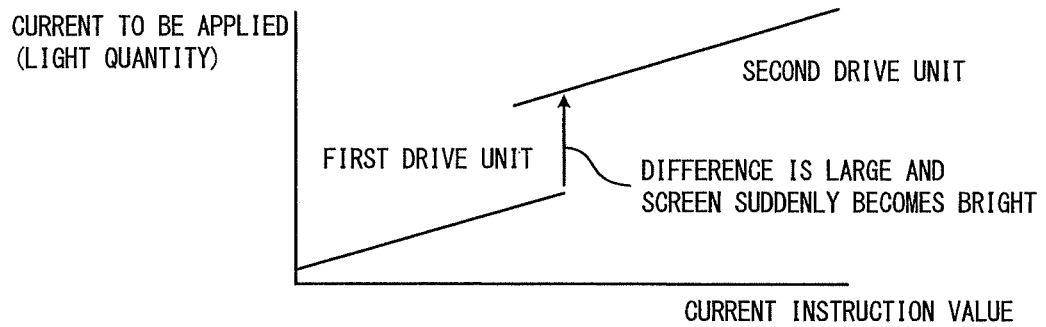
FIGS. 5A to 5C each are a graph showing a change in a light quantity when a first drive unit is switched to a second drive unit.
Figure 5B:
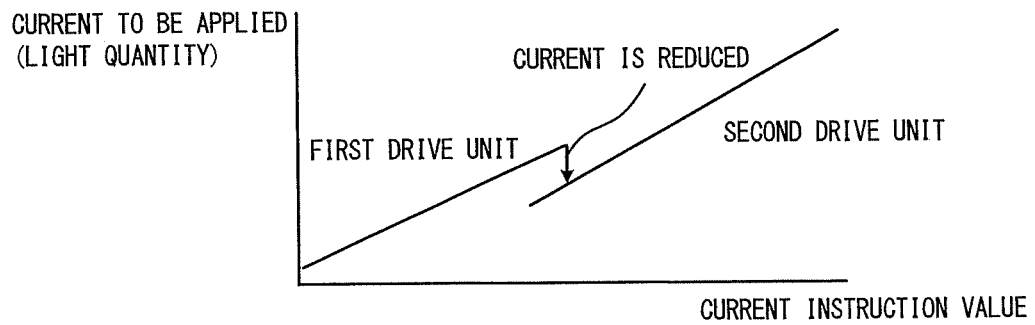
Figure 5C:
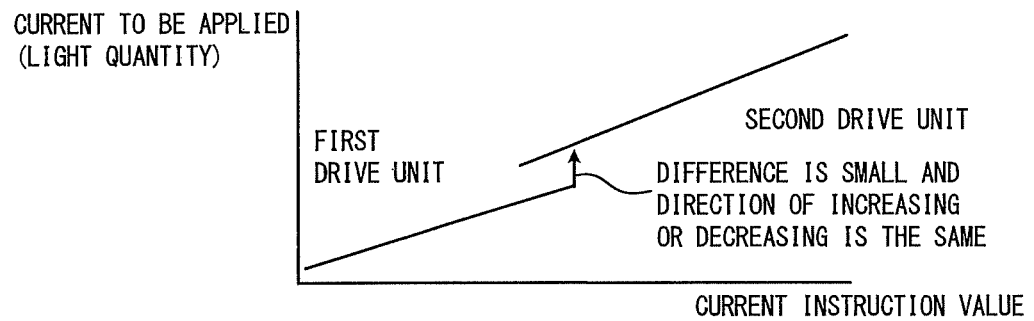

FIGS. 5A to 5C each are a graph showing a change in the light quantity when the first drive unit 201a is switched to the second drive unit 201b.

For example, it is assumed that the control unit 111 gradually changes the current instruction value in a direction of increasing the current, in the state in which the control unit 111 controls the first drive unit 201a to supply the current to the light source 112. In this case, when the current instruction value becomes the first current instruction value, the control unit 111 switches the drive unit 201 that supplies the current to the light source 112 from the first drive unit 201a to the second drive unit 201b. Here, the user who is viewing the captured image displayed on the monitor 104 may have an unnatural feeling, for example when a difference between the current applied to the light source 112 by the first drive unit 201a before the switching and the current applied to the light source 112 by the second drive unit 201b after the switching is large or the direction of increasing or decreasing the current is changed.

In an example shown in FIG. 5A, the current instruction value is gradually changed in the direction of increasing the current, and the current to be supplied to the light source 112 is greatly increased when the first drive unit 201a is switched to the second drive unit 201b at the first current instruction value. When the current to be supplied to the light source 112 thus increases rapidly when the drive unit 201 is switched, the light quantity of the light source 112 increases rapidly, and the user who is viewing the captured image displayed on the monitor 104 may have an unnatural feeling when the screen suddenly becomes bright. Therefore, it is preferable that the difference in the current caused when the first drive unit 201a is switched to the second drive unit 201b is at a level where the user cannot sense that the screen has suddenly become bright.

The difference in the ratio of the light quantity before change to after change that is within 5% does not generally cause human to have an unnatural feeling with respect to the change in the light quantity. Therefore, the relationship between the current instruction value and each output current of the first drive unit 201a and the second drive unit 201b may be defined so that, for example, when the first drive unit 201a is switched to the second drive unit 201b, a change in the light quantity (increase in the light quantity) when the current is output by the second drive unit 201b at the current instruction value at the time of switching falls within about 5% of the light quantity at the current associated with the current instruction value at the time of switching with respect to the first drive unit 201a.

To describe by replacing the above-described relationship between the light quantities with the relationship between the current values, the relationship between the current instruction value and each output current of the first drive unit 201a and the second drive unit 201b may be defined so that, for example, when the first drive unit 201a is switched to the second drive unit 201b, the current value output by the second drive unit 201b at the current instruction value at the time of switching has the magnitude within a predetermined acceptable range from the current value associated with the current instruction value at the time of switching with respect to the first drive unit 201a.

In an example shown in FIG. 5B, when the first drive unit 201a is switched to the second drive unit 201b, the current to be supplied to the light source 112 is reduced. In this case, it seems to the user who is viewing the monitor 104 that, for example, the screen gradually becomes bright while the first drive unit 201a is driven, becomes dark once at the time of switching, and then gradually becomes bright again while the second drive unit 201b is driven. When the control direction of the brightness of the screen is frequently switched in this way, the user may have the unnatural feeling. Therefore, it is preferable that the difference in the current caused when the first drive unit 201a is switched to the second drive unit 201b is at a level where the user does not aware that the screen has become dark.

There is an individual difference in a level where human can sense reversal of the change direction of the brightness. Therefore, in one embodiment, for the safety, it is necessary to prevent the change direction of the light quantity from being reversed at the time of switching. The relationship between the current instruction value and each output current of the first drive unit 201a and the second drive unit 201b may be defined so that, for example, when the first drive unit 201a is switched to the second drive unit 201b, the current value output by the second drive unit 201b at the current instruction value at the time of switching has the magnitude equal to or greater than the current value associated with the current instruction value at the time of switching with respect to the first drive unit 201a.

Additionally, the above-described relationships can be also used in combination. The relationship between the current instruction value and each output current of the first drive unit 201a and the second drive unit 201b may be defined so that, for example, when the first drive unit 201a is switched to the second drive unit 201b, the current value output by the second drive unit 201b at the current instruction value at the time of switching is equal to or greater than the current value associated with the current instruction value at the time of switching with respect to the first drive unit 201a, and the difference in the current value is equal to or less than about 5% in the light quantity ratio of the light quantity corresponding to the output current (FIG. 5C).

Note that the above-described relationship between the currents when the first drive unit 201a is switched to the second drive unit 201b may be established at the first instruction value, for example, or in another embodiment, it may be established at the current instruction value in a predetermined range around the first current instruction value, such as a range from the first current instruction value to the second current instruction value.

Figure 6A:
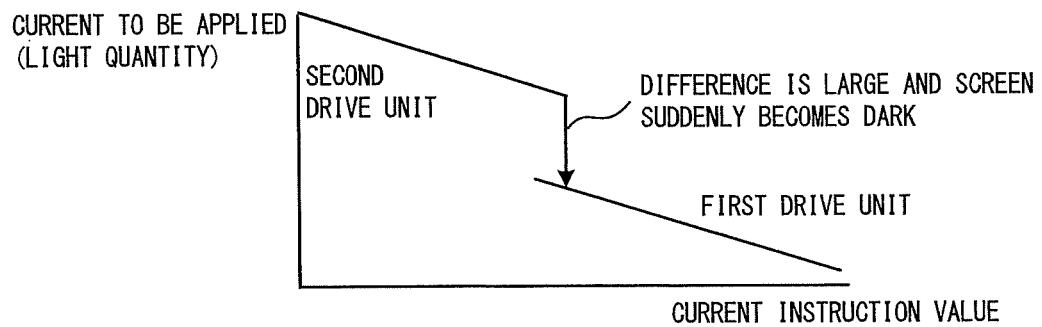
FIGS. 6A to 6C each are a graph showing a change in a light quantity when the second drive unit is switched to the first drive unit.

Subsequently, a change in the light quantity when the second drive unit 201b is switched to the first drive unit 201a will be described with reference to FIGS. 6A to 6C.

For example, it is assumed that the control unit 111 gradually changes the current instruction value in a direction of decreasing the current, in the state in which the control unit 111 controls the second drive unit 201b to supply the current to the light source 112. In this case, when the current instruction value becomes the second current instruction value, the control unit 111 switches the drive unit 201 that supplies the current to the light source 112 from the second drive unit 201b to the first drive unit 201a.

Figure 6B:
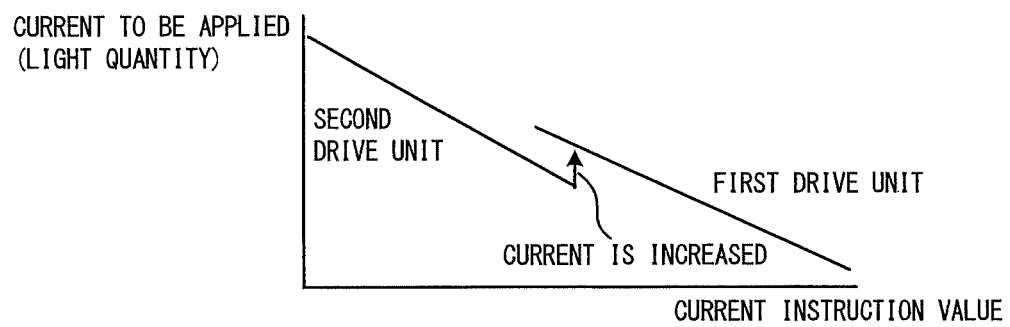
Figure 6C:
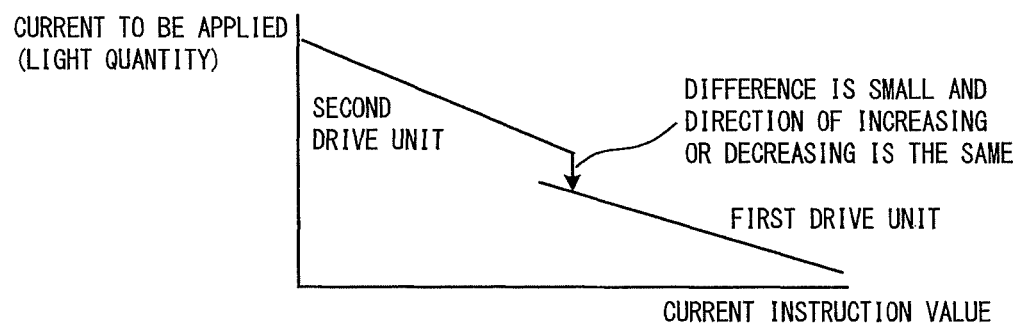

Also in this case, in the same manner as shown in FIGS. 5A to 5C, the user who is viewing the monitor 104 may have an unnatural feeling, for example when a difference between the current applied to the light source 112 by the second drive unit 201b before the switching and the current applied to the light source 112 by the first drive unit 201a after the switching is large (FIG. 6A) or the direction of increasing or decreasing the current is changed (FIG. 6B). Therefore, it is preferable that the difference in the light quantity caused when the second drive unit 201b is switched to the first drive unit 201a is at a level where the user cannot sense that the screen has suddenly become dark.

Then, the relationship between the current instruction value and each output current of the first drive unit 201a and the second drive unit 201b may be defined so that, for example, when the second drive unit 201b is switched to the first drive unit 201a, a change in the light quantity (decrease in the light quantity) when the current is output by the first drive unit 201a at the current instruction value at the time of switching is equal to or greater than about −5% of the light quantity at the current associated with the current instruction value at the time of switching with respect to the second drive unit 201b. To describe by replacing the relationship between the light quantities with the relationship between the current values, the relationship between the current instruction value and each output current of the first drive unit 201a and the second drive unit 201b may be defined so that, for example, when the second drive unit 201b is switched to the first drive unit 201a, the current value output by the first drive unit 201a at the current instruction value at the time of switching has the magnitude within a predetermined acceptable range from the current value associated with the current instruction value at the time of switching with respect to the second drive unit 201b.

Additionally, it is preferable that the difference in the current caused when the second drive unit 201b is switched to the first drive unit 201a is at a level where the user does not aware that the direction of increasing or decreasing the light quantity is changed at the time of switching and the screen has become bright. Therefore, in one embodiment, it is necessary to prevent the change direction of the light quantity from being reversed at the time of switching. The relationship between the current instruction value and each output current of the first drive unit 201a and the second drive unit 201b may be defined so that, for example, when the second drive unit 201b is switched to the first drive unit 201a, the current value output by the first drive unit 201a at the current instruction value at the time of switching has the magnitude equal to or less than the current value associated with the current instruction value at the time of switching with respect to the second drive unit 201b.

Additionally, the above-described relationships can be also used in combination. The relationship between the current instruction value and each output current of the first drive unit 201a and the second drive unit 201b may be defined so that, for example, when the second drive unit 201b is switched to the first drive unit 201a, the current output by the first drive unit 201a at the current instruction value at the time of switching is equal to or less than the current value associated with the current instruction value at the time of switching with respect to the second drive unit 201b, and the difference in the current value is equal to or less than about 5% in the light quantity ratio of the light quantity corresponding to the output current (FIG. 6C).

Additionally, the above-described relationship between the currents when the second drive unit 201b is switched to the first drive unit 201a may be established at the second current instruction value, for example, or in another embodiment, it may be established at the current instruction value in a predetermined range around the second current instruction value, such as a range from the second instruction value to the first current instruction value.

Note that the current value associated with the current instruction value with respect to the drive unit 201 does not necessarily fall within the range of the currents that can be output by the drive unit 201. For example, the relationship between the current and the current instruction value with respect to the drive unit 201 may have a correspondence relation indicating a predetermined tendency in the range of the currents that can be output by the drive unit 201, to have the correspondence relation indicated by straight lines in FIG. 4. The currents with respect to the current instruction values outside the range of the currents that can be output by the drive unit 201 can be also estimated by extending the correspondence relation to the current instruction value where the determination of the current value of the drive unit 201 is desired, for example.

For example, the correspondence relation between the current instruction value and the current value of the first drive unit 201a (for example, the first line segment 401 in FIG. 4) and the correspondence relation between the current instruction value and the current value of the second drive unit 201b (for example, the second line segment 402 in FIG. 4) may have a predetermined positional relationship. In one example, the predetermined positional relationship may be a positional relationship in which in the entire range or a partial range of the current instruction values, the current values associated with all of the current instruction values in the correspondence relation of the second drive unit 201b have a value equal to or greater than the current values associated with all of the current instruction values in the correspondence relation of the first drive unit 201a. In other words, the second line segment 402 may be positioned on the larger current side than the first line segment 401 in the entire range or the partial range of the current instruction values. Note that the correspondence relation between the current and the current instruction value is not limited to the straight line, and may be represented by the other relations such as the relation represented by the other functions, and the relation indicating the tendency represented by an approximate straight line.

Subsequently, the current instruction value output to the drive unit 201 by the control unit 111 will be described.

As described above, the control unit 111 of the light source device 101 obtains the current instruction value for specifying the current to be applied to the light source 112, based on the control information indicating the adjustment amount of the light quantity input from the video processor 103.

Then, the control unit 111 determines which of the first drive unit 201a and the second drive unit 201b is used to apply the current to the light source 112 based on the current instruction value at next timing specified based on the control information indicating the adjustment amount of the light quantity input from the video processor 103 and the currently selected drive unit 201.

For example, the control unit 111 may switch the drive unit 201 from the first drive unit 201a to the second drive unit 201b when the first drive unit 201a is currently selected to apply the current to the light source 112, and the current instruction value at the next timing specifies, for the first drive unit 201a, the current equal to or greater than the current value associated with the first current instruction value with respect to the first drive unit 201a.

On the other hand, for example, the control unit 111 may switch the drive unit 201 from the second drive unit 201b to the first drive unit 201a when the second drive unit 201b is currently selected to apply the current to the light source 112, and the current instruction value at the next timing specifies, for the second drive unit 201b, the current equal to or less than the current value associated with the second current instruction value with respect to the second drive unit 201b.

In other cases, the control unit 111 may apply the current to the light source 112 using the currently selected drive unit 201, for example. That is, for example, the control unit 111 does not necessarily switch the drive unit 201 when the first drive unit 201a is currently selected to apply the current to the light source 112, and the current instruction value at the next timing specifies, for the first drive unit 201a, the current less than the current value associated with the first current instruction value with respect to the first drive unit 201a. In addition, for example, the control unit 111 does not necessarily switch the drive unit 201 when the second drive unit 201b is currently selected to apply the current to the light source 112, and the current instruction value at the next timing specifies, for the second drive unit 201b, the current greater than the current value associated with the second current instruction value with respect to the second drive unit 201b.

Then, for example, when the drive unit 201 for outputting the current to the light source 112 is determined as described above, the control unit 111 transmits a signal to the driver 232 included in the determined drive unit 201 through the signal line 240, to select the drive unit 201. The control unit 111 outputs the current instruction value to the digital-analog converter 231 of the selected drive unit 201. In this case, the control unit 111 may output, to the selected drive unit 201, the current instruction value obtained based on the control information indicating the adjustment amount of the light quantity input from the video processor 103 as it is, or in another embodiment, the control unit 111 may convert the obtained current instruction value to the individual current instruction value according to the selected drive unit 201 (hereinafter referred to as an "individual current instruction value") and then output the converted value.

Figure 7:
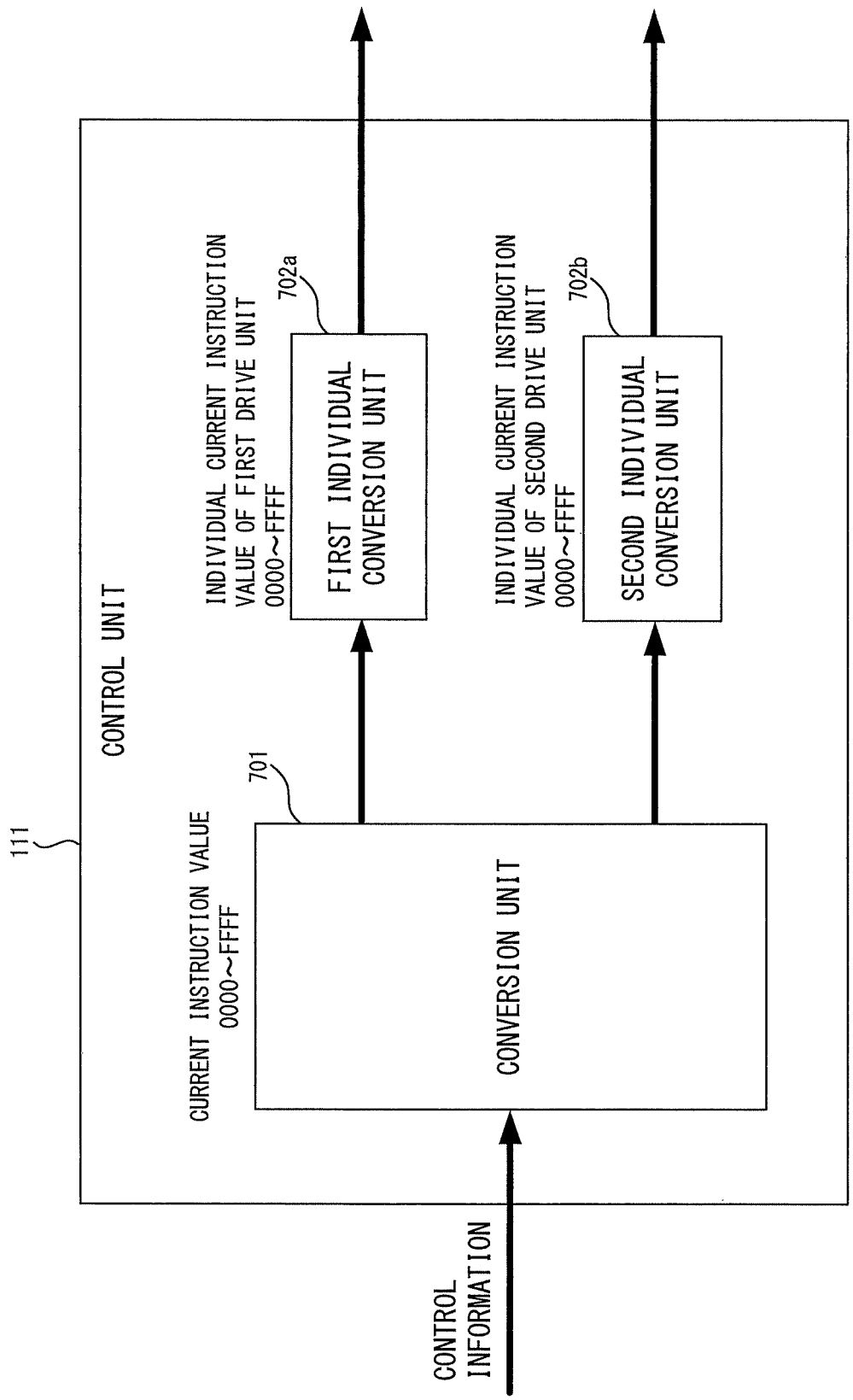
FIG. 7 is a diagram illustrating conversion to an individual current instruction value.

FIG. 7 is a diagram illustrating the conversion to the individual current instruction value. FIG. 7 illustrates the control unit 111, and the control unit 111 includes, for example, a conversion unit 701, a first individual conversion unit 702a, and a second individual conversion unit 702b. For example, when the control information indicating the adjustment amount of the light quantity is input from the video processor 103 to the control unit 111, the conversion unit 701 generates the current instruction value indicating the current to be applied to the light source 112 at the next timing, based on the input control information. Subsequently, the conversion unit 701 selects the drive unit 201 used for drive of the light source 112, based on the generated current instruction value.

For example, when the conversion unit 701 selects the first drive unit 201a, the conversion unit 701 outputs the current instruction value to the first individual conversion unit 702a. The first individual conversion unit 702a converts the current value indicated by the current instruction value input from the conversion unit 701 to the individual current instruction value specified in the first drive unit 201a, and outputs the converted value to the digital-analog converter 231a of the first drive unit 201a.

On the other hand, for example, when the conversion unit 701 selects the second drive unit 201b, the conversion unit 701 outputs the current instruction value to the second individual conversion unit 702b. The second individual conversion unit 702b converts the current value indicated by the current instruction value input from the conversion unit 701 to the individual current instruction value specified in the second drive unit 201b, and outputs the converted value to the digital-analog converter 231b of the second drive unit 201b.

Figure 8:
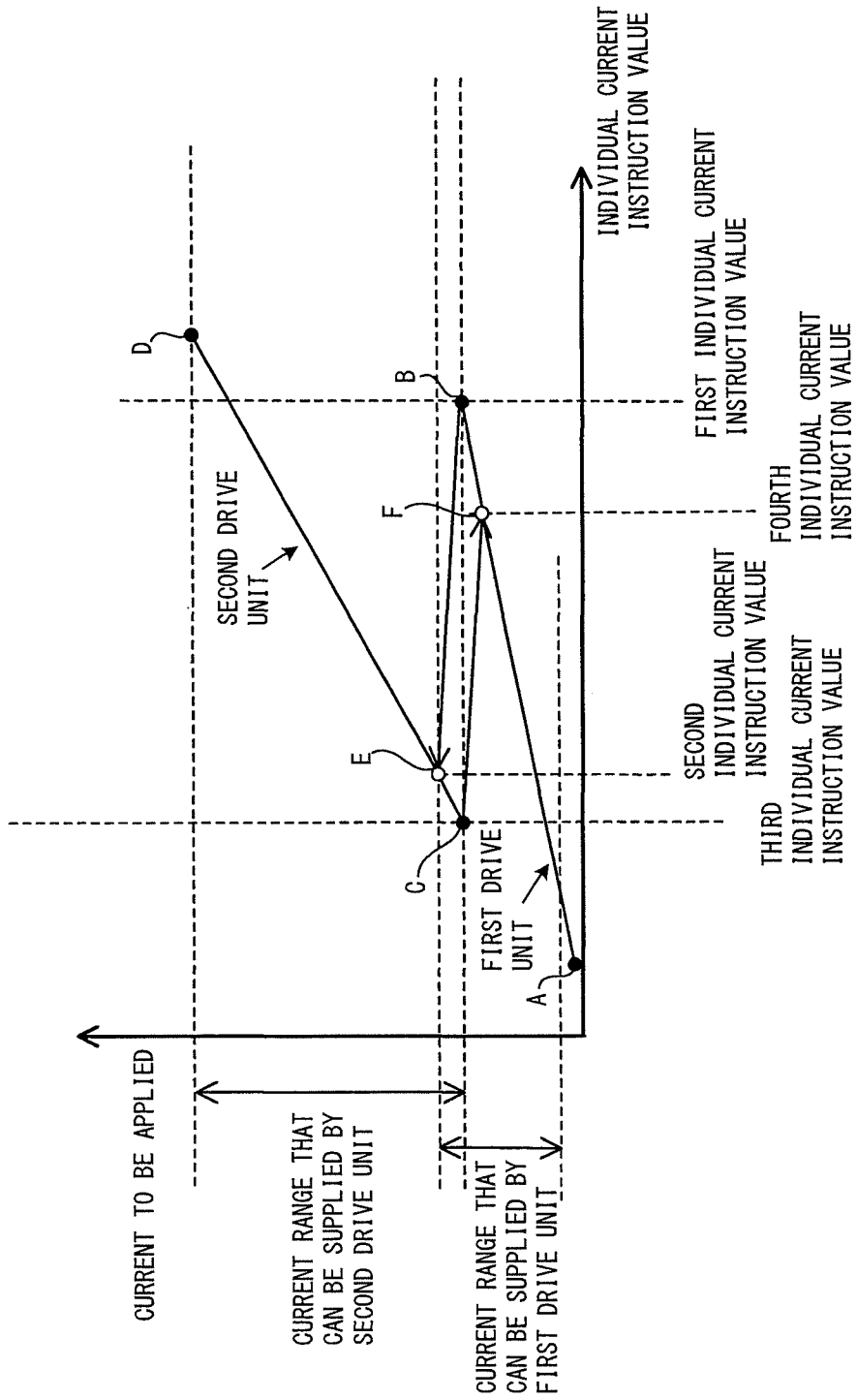
FIG. 8 is a plot showing a relationship between an individual current instruction value and a current to be applied of each of the first drive unit and the second drive unit.

FIG. 8 is a plot showing the relationship between the individual current instruction value and the current to be applied of each of the first drive unit 201a and the second drive unit 201b, in which the horizontal axis represents the individual current instruction value and the vertical axis represents the current to be applied. The individual current instruction value is a value associated with the current to be applied to the light source 112, and may be expressed by a digital value such as values in a range from 0000 to FFFF, for example. Note that the correspondence relation between the individual current instruction value and the current value may be individually set by each drive unit 201 of the first drive unit 201a and the second drive unit 201b, for example.

FIG. 8 shows, in the same graph, that a value in a nearest range of the individual current instruction value is assigned to each output current of the first drive unit 201a and the second drive unit 201b. Hereinafter, the case where the light quantity emitted from the light source 112 is changed from a small light quantity to a large light quantity will be described with reference to FIG. 8. In this case, the current to be applied to the light source 112 is changed from the small current to the large current.

When the light quantity is small, the control unit 111 selects the first drive unit 201a. When the current is increased, the individual current instruction value shortly becomes a first individual current instruction value (point B in FIG. 8) corresponding to the first current instruction value (point B in FIG. 4) at which the first drive unit 201a is switched to the second drive unit 201b. When the individual current instruction value becomes the first individual current instruction value corresponding to the first current instruction value, the control unit 111 switches the drive unit 201 from the first drive unit 201a to the second drive unit 201b. At this time, the individual current instruction value output to the second drive unit 201b is a second individual current instruction value (point E in FIG. 8) for specifying, in the second drive unit 201b, the current (current at the point E in FIG. 4) corresponding, on the second line segment 402 in FIG. 4, to the first current instruction value. Then, the control unit 111 shortly reaches the maximum current (point D in FIG. 8) when the current is monotonously increased.

Next, consider the case where the current is monotonously decreased from the maximum current. When the current is large, the control unit 111 selects the second drive unit 201b. When the control unit 111 changes the individual current instruction value with respect to the second drive unit 201b to gradually reduce the current, the individual current instruction value shortly reaches the second individual current instruction value (point E in FIG. 8). The control unit 111 changes the individual current instruction value to further reduce the current without performing any processing at the second individual current instruction value (point E in FIG. 8). Then, when the individual current instruction value with respect to the second drive unit 201b becomes a third individual current instruction value (point C in FIG. 8) corresponding to the second current instruction value in FIG. 4 (point C in FIG. 4), the control unit 111 switches the drive unit 201 from the second drive unit 201b to the first drive unit 201a. At this time, the individual current instruction value to the first drive unit 201a is a fourth individual current instruction value (point F in FIG. 8) for specifying, in the first drive unit 201a, the current (current at the point F in FIG. 4) corresponding, on the first line segment 401 in FIG. 4, to the second current instruction value. Then, the control unit 111 shortly reaches the minimum current (point A in FIG. 8) when the current is monotonously decreased.

As described above, for example, the control unit 111 outputs the individual current instruction value to each drive unit 201 using the first individual conversion unit 702a and the second individual conversion unit 702b, which performs the current control according to the embodiment.

Note that each individual current instruction value of the first drive unit 201a and the second drive unit 201b may be associated with the current instruction value and the current, to satisfy the relationship between the current instruction value and each output current of the first drive unit 201a and the second drive unit 201b at the time of switching, as described with reference to FIGS. 5A to 6C, for example.

There is an advantage that for example, the current generated by each drive unit 201 can be used at full scale by converting the current instruction value to the individual current instruction value for each selected drive unit 201. As described above, for example, when the light source device 101 includes a plurality of light sources 112, the control unit 111 controls to adjust the balance of the light quantity among the light sources 112 according to the observation mode, but such a control can be simplified by performing the conversion between the current instruction value and the individual current instruction value.

Note that in one embodiment, the storage unit 115 may store all or part of the following information. The control unit 111 may use the following information at the time of conversion between the current instruction value and the individual current instruction value, for example.

- The relationship between the individual current instruction value for each drive unit 201 and the current value to be applied to the light source 112
- The current value to be applied to the light source 112 at each of the first current instruction value and the second current instruction value
- The first to fourth individual current instruction values and the current value to be applied to the light source 112 at each of the first to fourth individual current instruction values
- The maximum current value to be applicable to the light source 112 and the current instruction value at that time
- The minimum current value to be applicable to the light source 112 and the current instruction value at that time Subsequently, a stop of current output from the drive unit 201 at the time of switching will be described. For example, it is assumed that one drive unit 201 of the first drive unit 201a and the second drive unit 201b is switched to the other drive unit 201. In this case, when the other drive unit 201 starts the current supply before the one drive unit 201 stops the current supply, about twice the current is temporarily supplied to the light source 112. As a result, the light quantity emitted from the light source 112 varies greatly, and which is therefore undesirable.

In the embodiment, the control unit 111 may provide, at the time of switching the drive unit 201, a predetermined stop time period during which each drive unit 201 does not supply the current to the light source 112, for example. For example, when one drive unit 201 is switched to the other drive unit 201, the control unit 111 causes the other drive unit 201 to start the current output to the light source 112 after the predetermined stop time period has elapsed since the stop of the current output from the one drive unit 201 to the light source 112. Controlling in this way makes it to possible to prevent the power from being supplied to the light source 112 from a plurality of drive units 201 at the same time at the time of switching. Note that the stop time period may be stored in the storage unit 115, for example.

Figure 9:
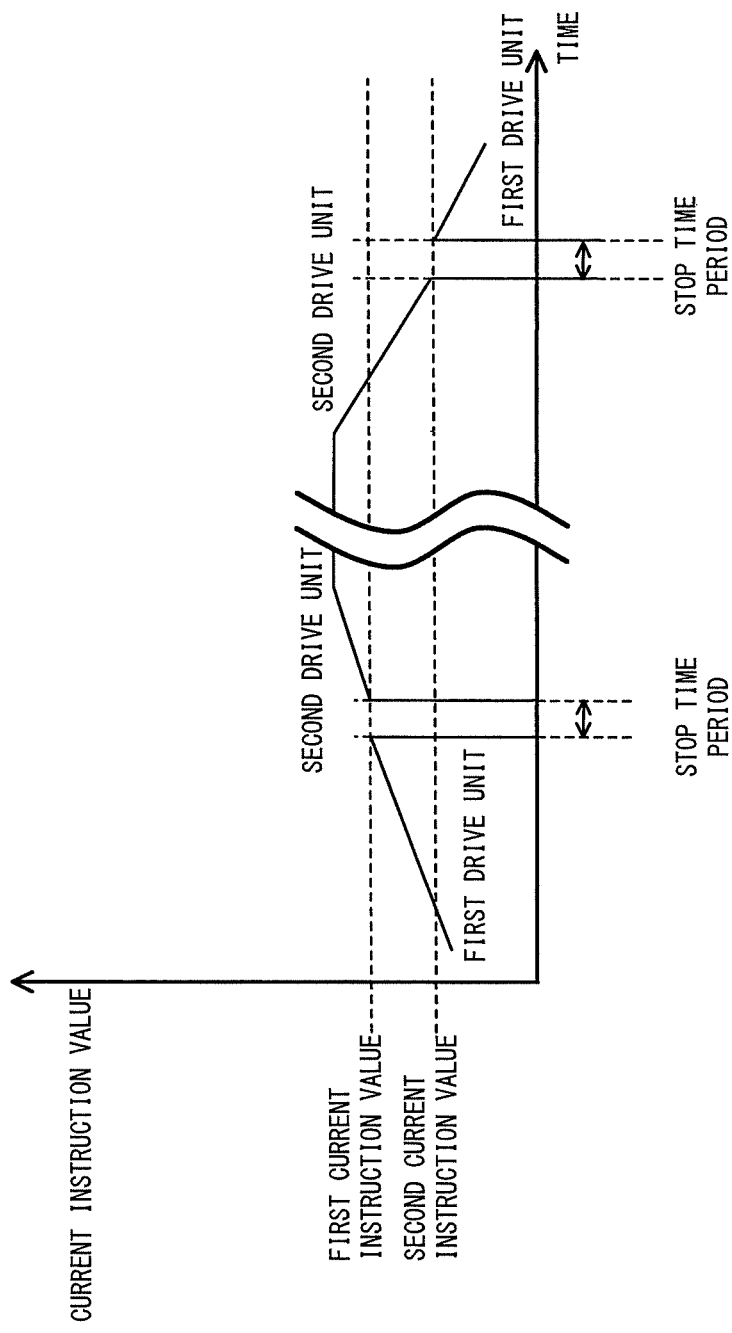
FIG. 9 is a graph showing an exemplary stop time period.

FIG. 9 is a graph showing an exemplary stop time period. FIG. 9 shows the relationship between the time in the time period including the switching timing of the drive unit 201 and the current instruction value, in which the horizontal axis represents the time and the vertical axis represents the current instruction value.

As shown in FIG. 9, when the current instruction value is gradually changed to increase the light quantity while the light source 112 is driven by the first drive unit 201a, the current instruction value shortly reaches the first current instruction value. Here, the control unit 111 switches the drive unit 201 from the first drive unit 201a to the second drive unit 201b. At this time, the control unit 111 first causes the first drive unit 201a to stop the current to the light source 112. Note that the current output of the first drive unit 201a may be stopped, for example, by outputting the current instruction value: 0000 for setting the output current to zero to the digital-analog converter 231a or by transmitting a stop signal to the driver 232a through the signal line 240a. An example in which the output of the current from the drive unit 201 is stopped is not limited thereto, and the other control may be performed so that the current is not supplied from the first drive unit 201a to the light source 112.

Next, for example, after the elapse of the predetermined stop time period, the control unit 111 outputs, to the digital-analog converter 231b, the second individual current instruction value for instructing the second drive unit 201b to output the current having the magnitude corresponding to the first current instruction value.

Also in the case where the light quantity of the light source 112 is reduced, the control unit 111 changes the current instruction value to reduce the current. The current instruction value shortly passes through the first current instruction value and reaches the second current instruction value. At this time, the control unit 111 stops the output of the current from the second drive unit 201b. Note that the current output of the second drive unit 201b may be stopped, for example, by outputting, to the digital-analog converter 231b, the current instruction value: 0000 for setting the output current to zero or by transmitting a stop signal to the driver 232b through the signal line 240b. Then, for example, after the elapse of the predetermined stop time period, the control unit 111 outputs, to the digital-analog converter 231a, the fourth individual current instruction value for instructing the first drive unit 201a to output the current having the magnitude corresponding to the second current instruction value.

As described above, FIG. 9 shows that at the switching, the current is output from the drive unit 201 that is selected after the switching, after the predetermined period of time has elapsed since the stop of the output of the current from the drive unit 201 that is selected before the switching. This makes it to possible to suppress that the current is applied to the light source 112 from the plurality of drive units 201 at the same time and the light quantity varies temporarily.

Note that, for example, the current instruction value may be constant for each frame of the image captured by the imaging element 125. In this case, the drive unit 201 may be switched in each frame.

FIG. 10 is a graph showing an example of the relationship between the imaging frame and the stop time period. The switching of drive unit 201 is performed between a first frame and a second frame, and the stop time period is provided therebetween. On the other hand, the stop time period may not be provided between the second frame and a third frame between which the drive unit 201 is not changed. For example, the stop time period may be set to a length at a predetermined ratio or less to be sufficiently shorter than an imaging time period of one frame by the imaging element 125. In one example, the stop time period may be set to 3 to 0.1% or less of the frame rate, and preferably 1% or less of the frame rate. In this way, the reduction in quantity of the light emitted per frame due to the stop time period can reduce the influence on the captured image, and in one example, it can be neglected.

Note that the length of the stop time period is preferably as short as possible within a range capable of preventing the current from being applied to the light source 112 from the plurality of drive units 201 at the same time, because the reduction in quantity of the light emitted per frame due to the stop time period can reduce the influence on the captured image. However, correcting the current instruction value by performing the following control enables the control that has no influence on the brightness of the image even when the stop time period is long.

For example, a corrected light quantity is determined so that an accumulated light quantity (for example: frame time period×light quantity) obtained by accumulating the light quantity emitted by the light source 112 over the time length of the frame in the case where there is no stop time period is equal to, within a predetermined error range, an accumulated light quantity (for example: (frame time period−stop time period)×corrected light quantity) obtained by accumulating the light quantity emitted by the light source 112 during the duration of the frame including the stop time period in the case where there is a stop time period. The control unit 111 outputs, to the drive unit 201 after the switching, the corrected current instruction value for specifying the current having the magnitude corresponding to the corrected light quantity thus determined, as the current instruction value in the frame including the stop time period, which enables the control that suppresses the influence on the brightness of the captured image even when the stop time period is long.

Figure 11:
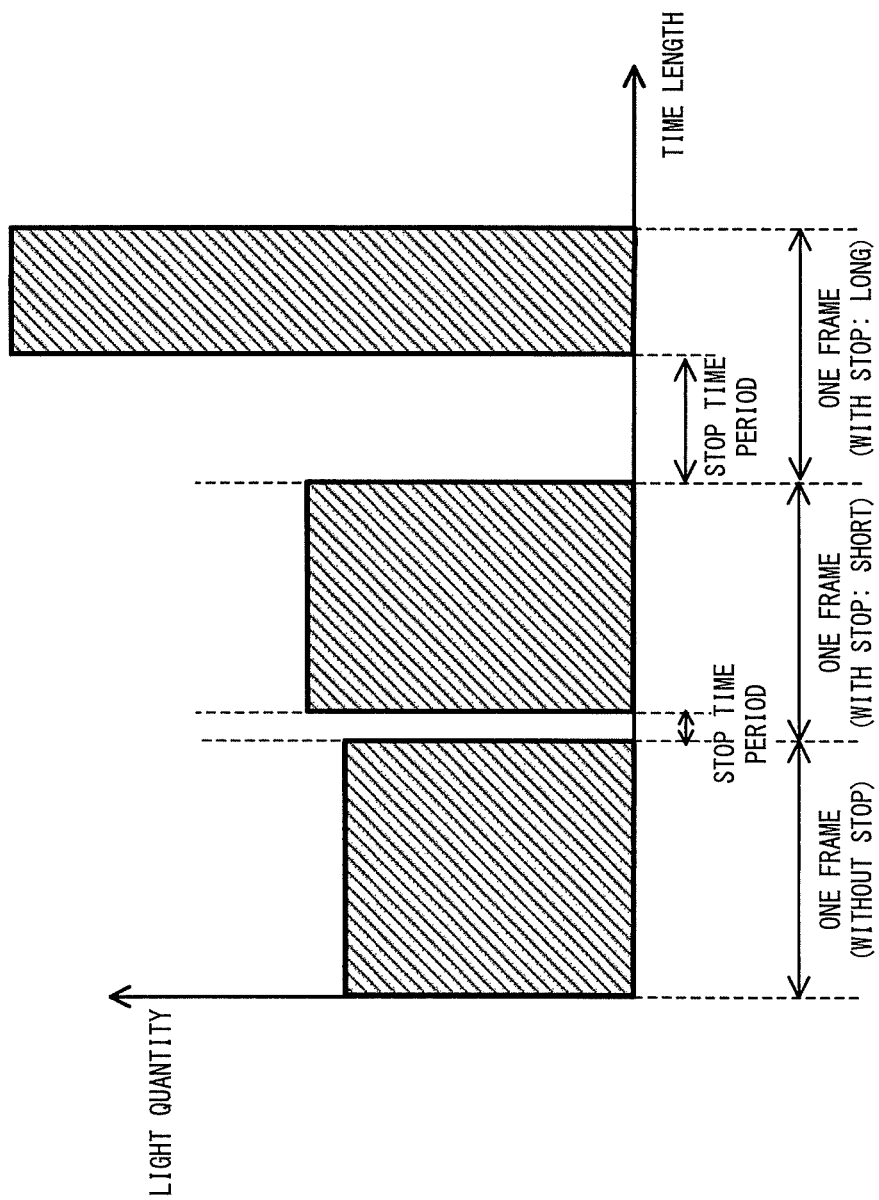
FIG. 11 is a graph showing an example of a length of the stop time period and a corrected light quantity.

FIG. 11 is a graph showing an example of a length of the stop time period and a change in the corrected light quantity according to the length of the stop time period. FIG. 11 shows three frames including a frame including no stop time period, a frame including a stop time period (short), and a frame including a stop time period (long), and the light quantities in these frames are set so that the areas of the shaded parts are equal to one another.

Subsequently, another embodiment is illustrated. For example, in the above description with reference to FIG. 4, an example is described in which the drive unit 201 is switched when the current instruction value becomes the first current instruction value or the second current instruction value. However, the embodiment is not limited thereto. For example, as described with reference to FIG. 10, the current instruction value may be a value fixed for each frame. For example, in such a case, the current instruction value at the next timing may be obtained by changing from the present current instruction value across the first current instruction value or the second current instruction value.

FIG. 12 is a graph showing an example of the switching control of the drive unit 201 when the current instruction value at the next timing is obtained by changing from the present current instruction value across the first current instruction value or the second current instruction value.

In FIG. 12, for example, it is assumed that the control unit 111 selects the first drive unit 201a, and the current instruction value is currently positioned at a point G in a state in which the current is output from the first drive unit 201a to the light source 112. At this time, a current instruction value X at the next timing obtained by the control unit 111 based on the control information from the video processor 103 may indicate, in the first drive unit 201a, a current equal to or greater than the current value of the first drive unit 201a corresponding to the first current instruction value. Here, the current instruction value X at the next timing indicates a position of a point H exceeding the current value (current value at the point B) corresponding to the first current instruction value. In this case, the control unit 111 switches the drive unit 201 from the first drive unit 201a to the second drive unit 201b. For example, the control unit 111 may stop the output of the current to the light source 112 from the first drive unit 201a, and may cause the second drive unit 201b to apply the current (current at a point I) corresponding to the current instruction value X to the light source 112.

In addition, for example, it is assumed that the control unit 111 selects the second drive unit 201b, and the current instruction value is currently positioned at a point J in a state in which the current is output from the second drive unit 201b to the light source 112. A current instruction value Y at the next timing obtained by the control unit 111 based on the control information from the video processor 103 may indicate, in the second drive unit 201b, a current equal to or less than the current value of the second drive unit 201b corresponding to the second current instruction value. Here, the current instruction value Y at the next timing indicates a position of a point K below the current value (current value at the point C) corresponding to the second current instruction value. In this case, the control unit 111 switches the drive unit 201 from the second drive unit 201b to the first drive unit 201a. For example, the control unit 111 may stop the output of the current to the light source 112 from the second drive unit 201b, and may cause the first drive unit 201a to apply the current (current at a point L) corresponding to the current instruction value Y to the light source 112.

In this way, the switching control of the drive unit 201 according to the embodiment can be also applied to the case where the current instruction value at the next timing is obtained by changing from the present current instruction value across the first current instruction value or the second current instruction value.

As described above, according to the embodiment, the light source device 101 supplies the current to the light source 112 while switching the plurality of drive units 201 that output the currents in different current ranges, whereby the light source device 101 can supply, to the light source 112, currents over a wide range of current values. For example, the current range corresponding to the range of the light quantity that can be output by the light source 112 cannot be covered by one drive unit 201 due to limitation on the hardware structure, in some cases. Also in this case, according to the embodiment, a plurality of drive units 201 are used to cause another drive unit 201 to supply currents in a current range that cannot be supplied by one drive unit 201, whereby the currents over a wide range of current values can be supplied to the light source 112. According to the embodiment, the switching of the drive unit 201 can suppress influence on the brightness of the captured image of the imaging element 125, for example.

Although the embodiment has been illustrated above, the embodiment is not limited to thereto. For example, the control unit 111 can be implemented on an FPGA, but may be implemented on a processor such as a microprocessor. In this case, the control unit 111 may function as the above-described control unit 111 by reading and executing the program stored in the storage unit 115.

For example, in the above-described embodiment, the light emitted by the light source 112 may be further controlled using PWM control. For example, in one embodiment, the drive unit 201 according to the above-described embodiment may be switched according to the current to be applied to the light source 112 while driving the light source 112 with a constant pulse width.

For example, the driver 232a of the first drive unit 201a and the driver 232b of the second drive unit 201b that are included in the light source drive unit 113 may have the same circuit configuration. Thus, the driver 232a and the driver 232b show the similar tendency with respect to a change in environment and a deterioration, and therefore this can suppress a large change in the relationship including a fact that the magnitude relationship such as switching conditions, and the like is reversed. Note that the driver 232a and the driver 232b may be disposed on the same surface on the same board, in one example. The light source device 101 may include a plurality of light source drive units 113 according to the number of the light sources 112. The plurality of light source drive units 113 may be configured so that a temperature difference between the driver 232a and the driver 232b in one light source drive unit 113 among the plurality of light source drive units 113 is equal to, within a predetermined error range, a temperature difference between the driver 232a and the driver 232b in the other light source drive unit 113.

In the above-described embodiment, an example has been described in which the control information is information indicating the adjustment amount of the light quantity obtained from the video processor 103 of the endoscope system 100, but the embodiment is not limited thereto. For example, the control information may be the other information that can be used for the adjustment of the light quantity of the light source 112, or may be acquired from the other device. For example, the control unit 111 may use, as the control information, a signal corresponding to the light quantity input from the optical sensor 250. Alternatively, the control unit 111 may receive the control information from the other device of the other system using the light source 112.

For example, in the process shown in FIG. 12, a difference may be large between the current value indicated by the current instruction value at the next timing obtained based on the control information and the current value indicated by the present current instruction value. In this case, the control unit 111 may output the current instruction value to gradually change the current, for example, to adjust the current value indicated by the current instruction value at the next timing over a plurality of frames such as three frames.

In one embodiment, the storage unit 115 may store all or part of the following information, for example. The control unit 111 may adjust the current instruction value to correct the influence received by the light source 112 due to the temperature change, the deterioration of the drive unit 201, or the like, using the following information, for example.

Information about temperature characteristics of the drive unit 201
Information about deterioration over time of the drive unit 201
Information about deterioration of the light source 112
Information about various control abnormalities Several embodiments have been described above. However, an embodiment is not limited to the embodiments described above, and it should be understood that the embodiment includes various modifications and alternatives of the embodiments described above. For example, it would be understood that various embodiments can be embodied by modifying components without departing from the spirit and scope of the embodiment. Furthermore, it should be understood that various embodiments may be implemented by appropriately combining a plurality of components disclosed in the embodiments described above. Moreover, those skilled in the art would understand that various embodiments can be implemented by deleting or replacing some components from all the components indicated in the embodiment or by adding some components to the components indicated in the embodiments.

What is claimed is:

1. A light source device comprising:
one or more control circuits configured to:
receive control information indicating an adjustment amount of light quantity for adjusting a brightness of an image captured by an imaging element to a predetermined brightness;
determine a current instruction value for specifying currents to be supplied by a plurality of drive circuits to a light source according to the control information,
cause a first drive circuit of the plurality of drive circuits to supply, to the light source, a first current according to the current instruction value;
switch from causing the first drive circuit to supply the first current to causing a second drive circuit of the plurality of drive circuits to supply, to the light source, a second current according to the current instruction value; and
at the time of switching provide a predetermined stop time period during which each of the plurality of drive circuits does not apply current to the light source.

2. The light source device according to claim 1,
wherein a first minimum current value to be output by the first drive circuit is smaller than a second minimum current value to be output by the second drive circuit, and
wherein a first maximum current value to be output by the first drive circuit is smaller than a second maximum current value to be output by the second drive circuit, and the first maximum current is larger than the second minimum current value.

3. The light source device according to claim 2,
wherein the one or more control circuits are configured to:
select any one of the first drive circuit and the second drive circuit based on the current instruction value; and
cause the one of the first drive circuit and the second drive circuit selected to supply, to the light source, one of the first current or the second current.

4. The light source device according to claim 3,
wherein the one or more control circuits are configured to:
convert the current instruction value to an individual current instruction value specified in the one of the first drive circuit and the second drive circuit; and
output to the one of the first drive circuit and the second drive circuit selected, the individual current instruction value obtained by the conversion.

5. The light source device according to claim 1, further comprising:
a storage device configured to store a first current instruction value,
wherein when the first drive circuit is caused to supply the first current to the light source and when the current instruction value is equal to or greater than the first current instruction value, the one or more control circuits are configured to:
stop the supply of the first current from the first drive circuit to the light source for the predetermined stop time period when the first current reaches the first current instruction value; and
cause the second drive circuit to supply the second current corresponding to the current instruction value to the light source after the predetermined stop time period.

6. The light source device according to claim 2, further comprising:
a storage device configured to store a first current instruction value,
wherein when the first drive circuit is caused to supply the first current to the light source and when the current instruction value is equal to or greater than the first current instruction value, the one or more control circuits are configured to:
  stop the supply of the first current from the first drive circuit to the light source for the predetermined stop time period when the first current reaches the first current instruction value; and
  cause the second drive circuit to supply the second current corresponding to the current instruction value to the light source after the predetermined stop time period.

7. The light source device according to claim 5,
wherein the storage device is further configured to store a second current instruction value that is smaller than the first current instruction value, and
wherein when the second drive circuit is caused to supply the second current to the light source and when the current instruction value is equal to or less than the second current instruction value, the one or more control circuits are configured to:
  stop the supply of the second current from the second drive circuit to the light source for the predetermined stop time period when the second current reaches the second current instruction value; and
  cause the first drive circuit to supply the first current having a magnitude corresponding to the second current instruction value to the light source after the predetermined stop time period.

8. The light source device according to claim 6,
wherein the storage device is further configured to store a second current instruction value that is smaller than the first current instruction value, and
wherein when the second drive circuit is caused to supply the second current to the light source and when the current instruction value is equal to or less than the second current instruction value, the one or more control circuits are configured to:
  stop the supply of the second current from the second drive circuit to the light source for the predetermined stop time period when the second current reaches the second current instruction value; and
  cause the first drive circuit to supply the first current having a magnitude corresponding to the second current instruction value to the light source after the predetermined stop time period.

9. The light source device according to claim 5,
wherein a second value of the second current at the first current instruction value is different from a first value of the first current at the first current instruction value.

10. The light source device according to claim 5,
wherein a second current value of the second current at the first current instruction value is equal to or greater than a first value of the first current at the first current instruction value.

11. The light source device according to claim 10,
wherein the second value at the first current instruction value is set within a predetermined acceptable range from the first current value at the first current instruction value.

12. The light source device according to claim 7,
wherein a first value of the first current at the second current instruction value is equal to or less than a second value of the second current at the second current instruction value.

13. The light source device according to claim 12,
wherein the first value at the second current instruction value is set within a predetermined acceptable range from the second value at the second current instruction value.

14. The light source device according to claim 7,
wherein a second value of the second current is at the second current instruction value is smaller than a first value of the first current at the first current instruction value.

15. The light source device according to claim 1,
wherein the one or more control circuits are configured to:
  determine the second current such that a second accumulated light quantity is equal to a first light quantity within a predetermined error range;
  the first accumulated light quantity is obtained by accumulating the light quantity emitted by the light source during a time length of a frame; and
  the second accumulated light quantity is obtained by accumulating the light quantity emitted by the light source during a time length of the frame including the predetermined stop time period.

16. An endoscope system comprising:
an endoscope; and
the light source device according to claim 1.

17. A control method for use with a light source device, the control method comprising:
  receiving control information indicating an adjustment amount of light quantity for adjusting a brightness of an image captured by an imaging element to a predetermined brightness;
  determining a current instruction value for specifying currents to be supplied by a plurality of drive circuits to a light source according to the control information,
  causing a first drive circuit of the plurality of drive circuits to supply, to the light source, a first current according to the current instruction value;
  switching from causing the first drive circuit to supply the first current to causing a second drive circuit of the plurality of drive circuits to supply, to the light source, a second current according to the current instruction value; and
  at the time of switching, providing a predetermined stop time period during which each of the plurality of drive circuits does not apply current to the light source.

18. The light source device according to claim 11, wherein the predetermined acceptable range is set such that the light quantity ratio is equal to or less than 5%, light quantity ratio is determined based on a first light quantity of the first current value and a second light quantity of the second current value.

19. The light source device according to claim 1, wherein a first current range to be supplied by first drive circuit is different from a second current range to be supplied by second drive circuit.

20. The light source device according to claim 1, wherein a part of the first current range overlaps a part of the second current range.

* * * * *